(12) United States Patent
Li et al.

(10) Patent No.: US 8,404,491 B2
(45) Date of Patent: Mar. 26, 2013

(54) LUMINESCENT CHEMICAL SENSOR INTEGRATED WITH AT LEAST ONE MOLECULAR TRAP

(75) Inventors: Zhiyong Li, Redwood City, CA (US); Michael Josef Stuke, Palo Alto, CA (US); Shih-Yuan Wang, Palo Alto, CA (US); Huei Pei Kuo, Cupertino, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 115 days.

(21) Appl. No.: 12/916,299

(22) Filed: Oct. 29, 2010

(65) Prior Publication Data

US 2012/0107948 A1 May 3, 2012

(51) Int. Cl.
*G01N 21/76* (2006.01)
(52) U.S. Cl. ..... 436/172; 436/80; 436/149; 422/186.13; 422/186.26
(58) Field of Classification Search .................. None
See application file for complete search history.

(56) References Cited

U.S. PATENT DOCUMENTS

| 7,731,827 | B2 | 6/2010 | Astorga-Wells et al. |
| 2009/0097022 | A1 | 4/2009 | Shen et al. |
| 2009/0136958 | A1 | 5/2009 | Gershow et al. |

OTHER PUBLICATIONS

Hu, M. et al. Gold nanofingers for molecule trpping and detection, 2010, Journal of American Chemical Society, 132(37), pp. 12820-12822.*
Bethlem, H.L., et al. Trapping polar molecules in an AC trap, 2006, Physical Review A, vol. 74, pp. 063403-1 063403-15.*

* cited by examiner

*Primary Examiner* — Robert Xu

(57) ABSTRACT

A luminescent chemical sensor integrated with at least one molecular trap. The luminescent chemical sensor includes at least one molecular trap and at least one metallic-nanofinger device integrated with at least one molecular trap. The molecular trap includes a plurality of electrodes that trap at least one analyte molecule. The metallic-nanofinger device includes a substrate, and a plurality of nanofingers coupled with the substrate. A nanofinger of the plurality includes a flexible column, and a metallic cap coupled to an apex of the flexible column. At least the nanofinger and a second nanofinger of the plurality of nanofingers are to self-arrange into a close-packed configuration with the analyte molecule. A method for using, and a chemical-analysis apparatus including the luminescent chemical sensor are also provided.

17 Claims, 16 Drawing Sheets

500A

1000A 

```
┌─────────────────────────────────────────────────┐
│ EXPOSE THE LUMINESCENT CHEMICAL SENSOR INTEGRATED│
│ WITH THE MOLECULAR TRAP TO A FLUID INCLUDING AN  │
│ ANALYTE MOLECULE                                 │
│                      1010                        │
└─────────────────────────────────────────────────┘
                        ↓
┌─────────────────────────────────────────────────┐
│ GENERATE AN ELECTRIC FIELD WITHIN THE MOLECULAR  │
│ TRAP                                             │
│                      1015                        │
└─────────────────────────────────────────────────┘
                        ↓
┌─────────────────────────────────────────────────┐
│ GUIDE AN ANALYTE MOLECULE BY THE ELECTRIC FIELD  │
│ INTO PROXIMITY WITH AT LEAST ONE NANOFINGER OF   │
│ THE METALLIC-NANOFINGER DEVICE                   │
│                      1020                        │
└─────────────────────────────────────────────────┘
                        ↓
┌─────────────────────────────────────────────────┐
│ TRAP THE ANALYTE MOLECULE WITH THE ELECTRIC FIELD│
│ IN PROXIMITY TO THE NANOFINGER                   │
│                      1025                        │
└─────────────────────────────────────────────────┘
                        ↓
┌─────────────────────────────────────────────────┐
│ ALLOW SUFFICIENT TIME FOR THE ANALYTE MOLECULE TO│
│ BIND TO THE METALLIC CAP OF THE NANOFINGER       │
│                      1030                        │
└─────────────────────────────────────────────────┘
                        ↓
┌─────────────────────────────────────────────────┐
│ ALLOW SUFFICIENT TIME FOR AT LEAST ONE NANOFINGER│
│ AND A SECOND NANOFINGER TO SELF-ARRANGE INTO A   │
│ CLOSE-PACKED CONFIGURATION WITH AT LEAST ONE     │
│ ANALYTE MOLECULE DISPOSED BETWEEN AT LEAST ONE   │
│ METALLIC CAP AND A SECOND METALLIC CAP OF THE    │
│ RESPECTIVE NANOFINGER AND SECOND NANOFINGER      │
│                      1035                        │
└─────────────────────────────────────────────────┘
```

FIG. 10A

LUMINESCENT CHEMICAL SENSOR INTEGRATED WITH AT LEAST ONE MOLECULAR TRAP

RELATED APPLICATIONS

This Application is related to PCT Patent Application, Serial Number PCT/US10/31790 by Zhiyong Li, et al., filed on Apr. 20, 2010, entitled "MULTI-PILLAR STRUCTURE FOR MOLECULAR ANALYSIS," and assigned to the assignee of the present invention. This Application is also related to PCT Patent Application, Serial Number PCT/US10/31809 by Zhiyong Li, et al., filed on Apr. 20, 2010, entitled "A SELF-ARRANGING, LUMINESCENCE-ENHANCEMENT DEVICE FOR SURFACE-ENHANCED LUMINESCENCE," and assigned to the assignee of the present invention. This Application is also related to PCT Patent Application, Serial Number PCT/US10/53304 by Zhiyong Li, et al., filed on Oct. 20, 2010, entitled "METALLIC-NANOFINGER DEVICE FOR CHEMICAL SENSING," and PCT Patent Application, Serial Number PCT/US10/53343 by Zhiyong Li, et al., filed on Oct. 20, 2010, entitled "LUMINESCENT CHEMICAL SENSOR INTEGRATED WITH METALLIC-NANOFINGER DEVICE FOR CHEMICAL SENSING," both also assigned to the assignee of the present invention.

TECHNICAL FIELD

Examples of the present invention relate generally to luminescent chemical sensors and molecular traps.

BACKGROUND

Chemical-sensing techniques that employ surface-enhanced luminescence, such as surface-enhanced Raman spectroscopy (SERS), have emerged as leading-edge techniques for the analysis of the structure of complex organic molecules, in particular, biomolecules and even biological cells, viruses and their macromolecular components. For example, in SERS, scientists engaged in the application of Raman spectroscopy have found that it is possible to enhance the intensity of a Raman spectrum of a molecule. For example, by decorating a surface, upon which a molecule is later adsorbed, with a thin layer of a metal, surface plasmons are generated that have frequencies in the range of electromagnetic radiation emitted by such a molecule that enhance the intensity of the Raman spectrum of the molecule.

In addition, spectroscopists utilizing spectroscopic techniques for the analysis of molecular structures have a continuing interest in improving the sensitivity of their spectroscopic techniques. Not only is increased sensitivity useful for reducing the time of analysis, but also increased sensitivity can provide previously unachievable results. For example, increased sensitivity is directly related to lower detectability limits for previously undetected molecular constituents. Thus, scientists engaged in the application of surface-enhanced luminescence techniques are motivated to increase the sensitivity of surface-enhanced luminescence techniques, for example, SERS, for the detection of molecules and the spectral signatures of moieties in these molecules.

DESCRIPTION OF THE DRAWINGS

The accompanying drawings, which are incorporated in and form a part of this specification, illustrate examples of the invention and, together with the description, serve to explain the examples of the invention:

FIG. 10A is a flowchart of a method for using a luminescent chemical sensor, in accordance with one or more examples of the present invention.

Figure 1:
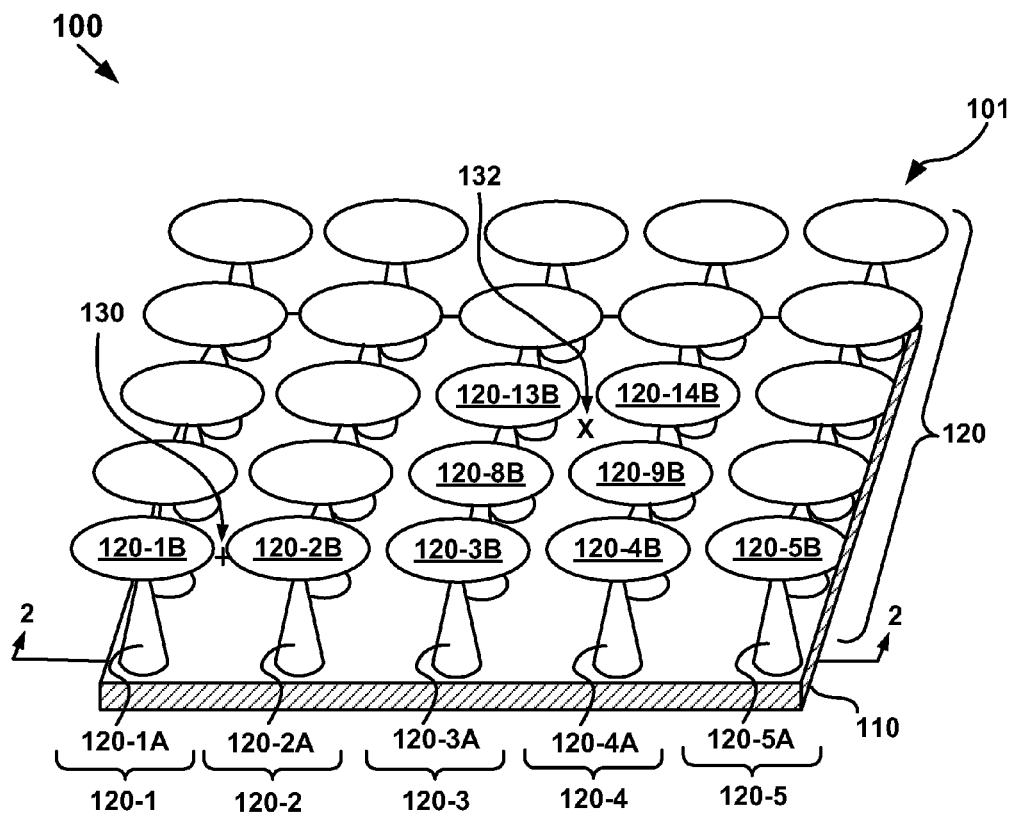
FIG. 1 is a perspective view of a metallic-nanofinger device for chemical sensing, in accordance with one or more examples of the present invention.

The drawings referred to in this description should not be understood as being drawn to scale except if specifically noted.

DESCRIPTION OF EXAMPLES

Reference will now be made in detail to the alternative examples of the present invention. While the invention will be described in conjunction with the alternative examples, it will be understood that they are not intended to limit the invention to these examples. On the contrary, the invention is intended to cover alternatives, modifications and equivalents, which may be included within the spirit and scope of the invention as defined by the appended claims.

Furthermore, in the following description of examples of the present invention, numerous specific details are set forth in order to provide a thorough understanding of the present invention. However, it should be noted that examples of the present invention may be practiced without these specific details. In other instances, well known methods, procedures, and components have not been described in detail as not to unnecessarily obscure examples of the present invention. Throughout the drawings, like components are denoted by like reference numerals, and repetitive descriptions are omitted for clarity of explanation if not necessary.

Examples of the present invention include a luminescent chemical sensor integrated with at least one molecular trap. The luminescent chemical sensor includes at least one molecular trap and at least one metallic-nanofinger device integrated with at least one molecular trap. The molecular trap includes a plurality of electrodes. The electrodes are to trap at least one analyte molecule. The metallic-nanofinger device includes a substrate, and a plurality of nanofingers coupled with the substrate. A nanofinger of the plurality includes a flexible column, and a metallic cap coupled to an apex of the flexible column. At least the nanofinger and a second nanofinger of the plurality of nanofingers are to self-arrange into a close-packed configuration with at least one analyte molecule. A method for using, and a chemical-analysis apparatus including the luminescent chemical sensor are also provided.

The individual components of the luminescent chemical sensor, viz., the metallic-nanofinger device and the molecular trap are first described, before describing their integration into the luminescent chemical sensor, beginning with the description of the metallic-nanofinger device, as next described.

With reference now to FIG. 1, in accordance with one or more examples of the present invention, a perspective view 100 is shown of a component of a luminescent chemical sensor 701 (see FIGS. 7A-7D), a metallic-nanofinger device 101 for chemical sensing, examples of which are subsequently described in detail, before commencing the description of the luminescent chemical sensor 701. The metallic-nanofinger device 101 that provides for surface-enhanced luminescence includes a substrate 110, and a plurality 120 of nanofingers, for example, nanofingers 120-1, 120-2, 120-3, 120-4 and 120-5. The nanofinger 120-1 of the plurality 120 includes the flexible column 120-1A, and the metallic cap 120-1B. Similarly, other nanofingers, for example, nanofingers 120-2, 120-3, 120-4 and 120-5, of the plurality 120 include flexible columns, for example, flexible columns 120-2A, 120-3A, 120-4A and 120-5A, respectively, and metallic caps, for example, metallic caps 120-2B, 120-3B, 120-4B and 120-5B, respectively. As shown in FIG. 1, by way of example, a row of nanofingers includes nanofingers 120-1, 120-2, 120-3, 120-4 and 120-5, without limitation thereto; and, by way of example, an array of nanofingers includes several rows, without limitation thereto. Thus, in accordance with one example of the present invention, the plurality 120 of nanofingers includes the array of nanofingers including several rows of nanofingers. However, other arrangements of nanofingers that are less well-ordered than shown in FIG. 1 are also within the spirit and scope of examples of the present invention. The arrangement shown in FIG. 1 is illustrative of but one example of an arrangement of the plurality 120 of nanofingers in a metallic-nanofinger device 101 as may be fabricated in a top-down fabrication procedure, which employs a reticulated mask in a photolithographic process; but, other methods of fabrication are also within the spirit and scope of examples of the present invention, which are subsequently described. Moreover, the morphology of the metallic caps may differ from that shown in FIG. 1; for example, the morphology of the metallic caps may be substantially spherical, or alternatively, truncated substantially spherical, in accordance with one or more examples of the present invention, which are also subsequently described.

With further reference to FIG. 1, in accordance with one or more examples of the present invention, a top portion including a metallic cap of a nanofinger, for example, nanofinger 120-1, of the plurality 120 of nanofingers may have the shape of an ellipsoid. However, in accordance with one or more examples of the present invention, a top portion including a metallic cap of a nanofinger is not limited to having the shape of an ellipsoid, as other shapes, in particular spheres, are also within the spirit and scope of examples of the present invention.

Figure 4:
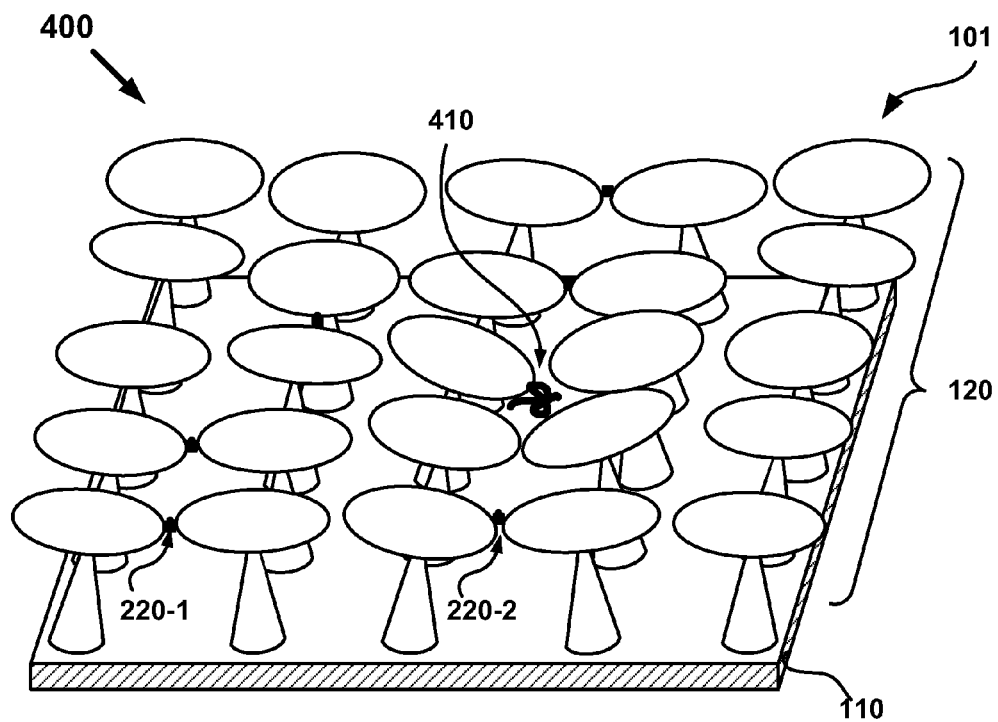
FIG. 4 is another perspective view of the metallic-nanofinger device for chemical sensing of FIG. 1 after the nanofingers have self-arranged into close-packed configurations with molecules disposed between the metallic caps, in accordance with one or more examples of the present invention.

With further reference to FIG. 1, by way of example, in accordance with one or more examples of the present invention, the flexible columns may have the form of nanocones, as shown in FIGS. 1 and 4, without limitation thereto; but, more generally, the flexible columns may be selected from the group consisting of: nanocones, nanopyramids, nanorods, nanobars, nanopoles and nanograss, without limitation thereto. As used herein, the terms of art, "nanocones," "nanopyramids," "nanorods," "nanobars," "nanopoles" and "nanograss," refer to structures that are substantially: conical, pyramidal, rod-like, bar-like, pole-like and grass-like, respectively, which have nano-dimensions as small as a few tens of nanometers (nm) in height and a few nanometers in diameter, or width. For example, flexible columns may include nanocolumns having the following dimensions: a diameter of 50 nm to 500 nm, a height of 50 nm to 2 micrometers (μm), and a gap between flexible columns of 20 nm to 500 nm. The terms of art, "substantially conical," "substantially pyramidal," "substantially rod-like," "substantially bar-like," "substantially pole-like" and "substantially grass-like," means that the structures have nearly the respective shapes of cones, pyramids, rods, bars, poles and grass-like asperities within the limits of fabrication with nanotechnology.

With further reference to FIG. 1, by way of example, in accordance with one or more examples of the present invention, the metallic caps may have the form of oblate nanoellipsoids, as shown in FIGS. 1 and 4, without limitation thereto; but, more generally, the metallic caps may be selected from the group consisting of: nanospheres, prolate nanoellipsoids, oblate nanoellipsoids, nanodisks, and nanoplates, without limitation thereto. As used herein, the terms of art, "nanospheres," "prolate nanoellipsoids," "oblate nanoellipsoids," "nanodisks," and "nanoplates," refer to structures that are substantially: spherical, prolate ellipsoidal, oblate ellipsoidal, disk-like, and plate-like, respectively, which have nano-dimensions as small as a few nanometers in size: height, diameter, or width. For example, in accordance with one or more examples of the present invention, the diameter of the metallic caps is on the order of 20 nm to 500 nm. In addition, the terms of art, "substantially spherical," "substantially prolate ellipsoidal," "substantially oblate ellipsoidal," "substantially disk-like," and "substantially and plate-like," means that the structures have nearly the respective shapes of spheres, prolate ellipsoids, oblate ellipsoids, disks, and plates within the limits of fabrication with nanotechnology.

With further reference to FIG. 1, in accordance with one or more examples of the present invention, the metallic cap 120-1B is coupled to an apex 120-1C (not shown in FIG. 1, but see FIGS. 5B and 5C) of the flexible column 120-1A. Similarly, other metallic caps, for example, metallic caps 120-2B, 120-3B, 120-4B and 120-5B, are coupled to apices, for example, apices 120-2C, 120-3C, 120-4C and 120-5C, respectively, (not shown in FIG. 1, but see FIGS. 5B and 5C) of flexible columns, for example, flexible columns 120-2A, 120-3A, 120-4A and 120-5A, respectively. As shown in FIG. 1, a plurality of interstices is disposed between the plurality 120 of nanofingers. For example, a small interstice 130 is located between metallic cap 120-1B and metallic cap 120-2B. By way of further example, an interstice of a different kind, a large interstice 132, is located between four metallic caps 120-8B, 120-9B, 120-13B and 120-14B. Such interstices are to receive analyte molecules (not shown, but see FIG. 2) for the purpose of surface-enhanced luminescence. As used herein, the term of art, "surface-enhanced luminescence," also embraces within the scope of its meaning surface-enhanced Raman emission, as in surface-enhanced Raman spectroscopy (SERS), surface-enhanced reflectivity, surface-enhanced light scattering, and surface-enhanced fluorescence. In accordance with one or more examples of the present invention, at least the nanofinger 120-1 and a second nanofinger 120-2 of the plurality 120 are to self-arrange into a close-packed configuration with at least one analyte molecule 220-1 (not shown, but see FIG. 2) disposed between at least the metallic cap 120-1B and a second metallic cap 120-2B of respective nanofinger 120-1 and second nanofinger 120-2, for example, at the location of the small interstice 130, as is next described with the aid of a cross-section through line 2-2.

Figure 2:
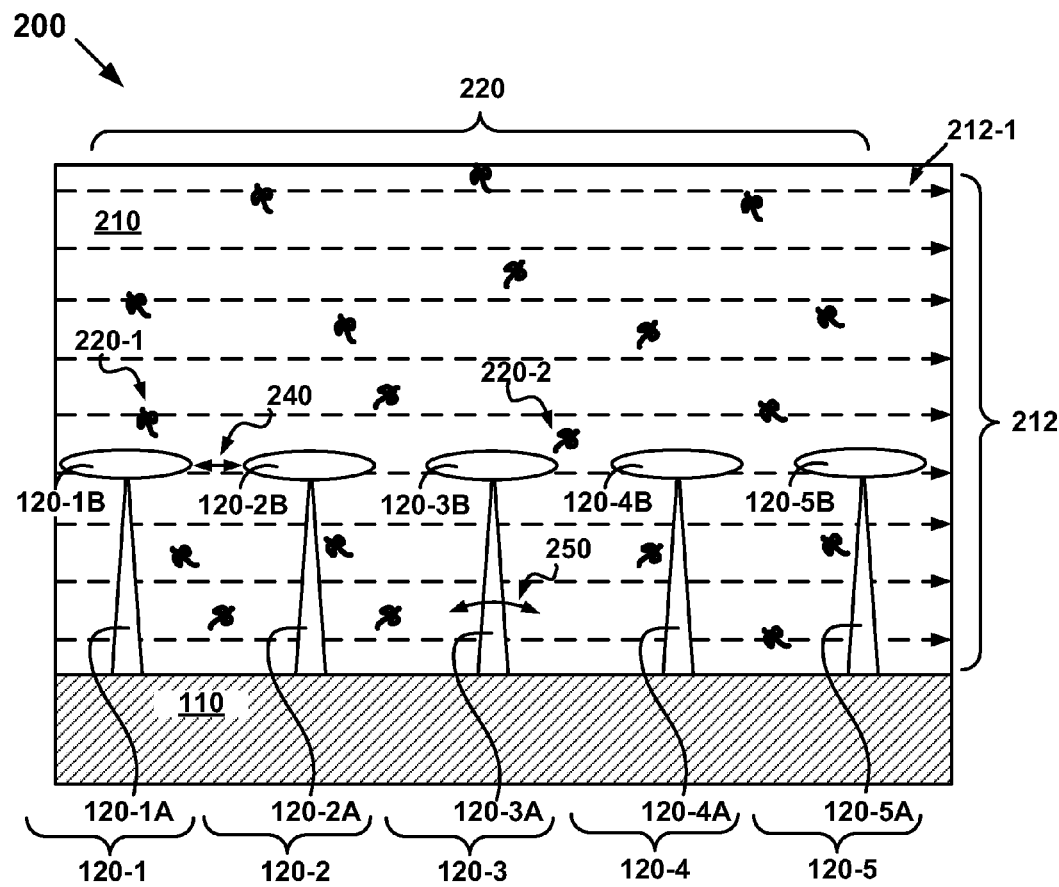
FIG. 2 is a cross-sectional elevation view, through line 2-2 of FIG. 1, of the metallic-nanofinger device for chemical sensing in contact with a fluid, for example, a liquid, carrying a plurality of molecules, in accordance with one or more examples of the present invention.

With reference now to FIG. 2, in accordance with one or more examples of the present invention, a cross-sectional elevation view 200 is shown of the metallic-nanofinger device 101 for chemical sensing through line 2-2 of FIG. 1. FIG. 2 shows a row of nanofingers 120-1, 120-2, 120-3, 120-4 and 120-5 in profile; nanofingers 120-1, 120-2, 120-3, 120-4 and 120-5 include flexible columns 120-1A, 120-2A, 120-3A, 120-4A and 120-5A, and metallic caps 120-1B, 120-2B, 120-3B, 120-4B and 120-5B, respectively. As shown in FIG. 2, the range of flexibility of each of the flexible columns 120-1A, 120-2A, 120-3A, 120-4A and 120-5A is indicated by the example double headed arrow 250, which is shown overlaying flexible column 120-3A. As further shown in FIG. 2, the row of nanofingers 120-1, 120-2, 120-3, 120-4 and 120-5 of the metallic-nanofinger device 101 is to come into contact with a fluid 212 carrying a plurality 220 of analyte molecules, for example, analyte molecules 220-1 and 220-2. The fluid 212 may be either a liquid, or a gas. By way of example, as shown in FIG. 2, the fluid may be in motion, without limitation thereto, as indicated by flow vectors, of which flow vector 212-1 is an example; such a configuration might be suitable for sampling an environment with the metallic-nanofinger device 101 for the presence of a target molecule, also referred to herein as a "target," without limitation thereto.

With further reference to FIG. 2, as used herein, the term of art, "molecule," may be used to refer to the smallest unit of an element consisting of one or more like atoms, the smallest unit of a compound consisting of one or more like or different atoms, and more generally to any very small particle, for example, a biological cell, a virus, or molecular component of a biological cell or a virus. For example, an analyte molecule may include the following molecular species: proteins, antibodies, antigens, deoxyribonucleic acids (DNAs), ribonucleic acids (RNAs), organic molecules, biopolymers, polymers, and segments of the same. Also, as used herein the term of art, "target," also includes an analyte molecule selected from the group consisting of molecules, organic molecules, biomolecules, biological cells, viruses and the molecular components of biological cells and viruses. Alternatively, the fluid may be static without motion, as might be the case for immersion of the metallic-nanofinger device 101 in a solution containing an analyte including a liquid and molecules, also more generally analyte molecules, of which the analyte is composed; alternatively, the fluid may be an aerosol including a gas with a plurality of analyte molecules, or particles. Thus, the metallic-nanofinger device 101 is to receive molecules, also more generally analyte molecules, of an analyte for spectroscopic analysis as is SERS, surface-enhanced fluorescence spectroscopy, surface-enhanced reflectivity, surface-enhanced light scattering, or other surface-enhanced luminescence applications.

With further reference to FIG. 2, in accordance with one or more examples of the present invention, an analyte molecule 220-1 may approach the site of an interstice, for example, small interstice 130, where adjacent metallic caps, for example, metallic caps 120-1B and 120-2B, are separated by a distance 240. In accordance with an example of the present invention, a metallic cap, for example, metallic cap 120-1B, of the plurality 120 of nanofingers is to bind to a analyte molecule 220-1 disposed in close proximity to the metallic cap 120-1B. By way of example, such binding may occur through Van der Waals forces between the metallic cap 120-1B and the analyte molecule 220-1, without limitation thereto; or alternatively, such binding may occur through other types of binding forces, such as surface physisorption or surface chemisorption of the molecule by the metallic cap 120-1B, without limitation thereto. Once the molecule is bound to the metallic cap, for example, metallic cap 120-1B, in accordance with an example of the present invention, at least one metallic cap, for example, metallic cap 120-1B, of a plurality 530 (see FIG. 5C) of metallic caps is to enhance luminescence from the analyte molecule 220-1 disposed in close proximity to the metallic cap 120-1B. Moreover, in accordance with another example of the present invention, at least one metallic cap, for example, metallic cap 120-1B, of the plurality 530 (see FIG. 5C) of metallic caps may be composed of a constituent that enhances surface luminescence, such as a material selected from the group consisting of copper, silver, aluminum and gold, or any combination of copper, silver, aluminum and gold. Furthermore, in accordance with another example of the present invention, the flexible columns 120-1A, 120-2A, 120-3A, 120-4A and 120-5A of the plurality 120 of nanofingers 120-1, 120-2, 120-3, 120-4 and 120-5 further include a flexible material selected from the group, which includes both dielectric and non-dielectric materials, consisting of a highly cross-linked uv-curable or thermal-curable polymer, a highly cross-linked uv-curable or thermal-curable plastic, a polysiloxane compound, silicon, silicon dioxide, spin-on glass, a sol-gel material, silicon nitride, diamond, diamond-like carbon, aluminum oxide, sapphire, zinc oxide, and titanium dioxide, the purpose of which is next described.

Figure 3:
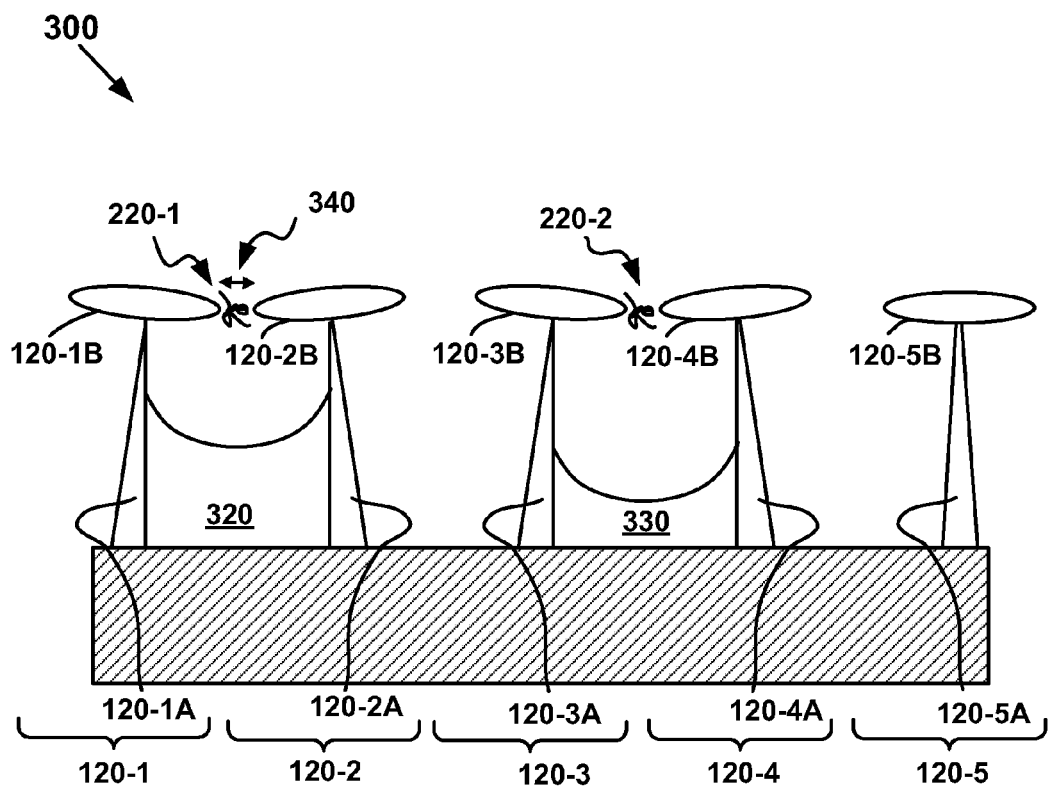
FIG. 3 is a cross-sectional elevation view, through line 2-2 of FIG. 1, of the metallic-nanofinger device for chemical sensing that shows nanofingers self-arranging into close-packed configurations with molecules disposed between metallic caps of nanofingers, in accordance with one or more examples of the present invention.

With reference now to FIG. 3, in accordance with one or more examples of the present invention, a cross-sectional elevation view 300 is shown of the metallic-nanofinger device 101 for chemical sensing through line 2-2 of FIG. 1. FIG. 3 shows nanofingers 120-1, 120-2, 120-3 and 120-4 self-arranging into close-packed configurations with analyte molecules, for example, analyte molecule 220-1, disposed between metallic caps 120-1B and 120-2B of the nanofingers 120-1 and 120-2, respectively, and analyte molecule 220-2, disposed between metallic caps 120-3B and 120-4B of the nanofingers 120-3 and 120-4, respectively. Because the flexible columns 120-1A, 120-2A, 120-3A and 120-4A of the plurality 120 of nanofingers include a flexible, or compliant, material as described above, in accordance with an example of the present invention, at least one flexible column 120-1A is arranged to bend towards at least a second flexible column 120-2A, and to dispose the analyte molecule 220-1 in close proximity with at least a second metallic cap 120-2B on the second flexible column 120-2A. For the case when the fluid is a liquid, liquid pools 320 and 330, may remain trapped between the flexible columns, for example, flexible columns 120-1A and 120-2A, and flexible columns 120-3A and 120-4A, respectively, which give rise to microcapillary forces exerted upon the flexible columns; the microcapillary forces serve to draw together the flexible columns, for example, flexible columns 120-1A and 120-2A, and flexible columns 120-3A and 120-4A, as the liquid evaporates, which allows the nanofingers 120-1 and 120-2 to self-arrange into a close-packed configuration with at least one analyte molecule 220-1 disposed between at least the metallic cap 120-1B and a second metallic cap 120-2B of respective nanofinger 120-1 and second nanofinger 120-2. For the case when the fluid is a gas, other forces may come into play, or be applied to the plurality 120 of nanofingers, allowing the nanofingers 120-1 and 120-2 to self-arrange into a close-packed configuration with at least one analyte molecule 220-1 disposed between at least the metallic cap 120-1B and a second metallic cap 120-2B of respective nanofinger 120-1 and second nanofinger 120-2.

Thus, with further reference to FIG. 3, in accordance with one or more examples of the present invention, the flexible column 120-1A is to bend towards the second flexible column 120-2A under action of microcapillary forces induced by removal of fluid carrier 210 provided to carry the analyte molecule 220-1 into proximity with the metallic cap 120-1B and second metallic cap 120-2B. In accordance with another example of the present invention, a spacing 340 of the close-packed configuration between the metallic cap 120-1B and second metallic cap 120-2B with a analyte molecule 220-1 disposed between the metallic cap 120-1B and second metallic cap 120-2B is determined by a balance of binding forces, between the analyte molecule 220-1 and the metallic cap 120-1B and second metallic cap 120-2B, with restoring forces exerted by the flexible column 120-1A and second flexible column 120-2A due to displacement of the flexible column 120-1A and second flexible column 120-2A towards the analyte molecule 220-1. Thus, in accordance with an example of the present invention, the spacing 340 approaches a limit determined by the size of the analyte molecule 220-1, which may be as small as 0.5 nm. The spacing 340 approaches the physical limit of the smallest possible separation between metallic caps 120-1B and 120-2B; and, thus, the metallic caps act as two antennas approaching the largest coupling that may be possible between at least two such antennas for surface-enhanced luminescence. Moreover, the effect of coupling more than two antennas is also within the spirit and scope examples of the present invention, which is next described.

With reference now to FIG. 4 and further reference to FIGS. 1 and 3, in accordance with one or more examples of the present invention, another perspective view 400 is shown of the metallic-nanofinger device 101 for chemical sensing of FIG. 1. As shown in FIG. 4, most of the nanofingers of the plurality 120 have self-arranged into close-packed configurations with analyte molecules, for example, analyte molecules 220-1, 220-2 and 410, disposed between the metallic caps, for example, metallic caps 120-1B and 120-2B, metallic caps 120-3B and 120-4B, and metallic caps 120-8B, 120-9B, 120-13B and 120-14B, respectively. In accordance with one or more examples of the present invention, the corresponding flexible columns coupled with the metallic caps have bent towards adjacent flexible columns, as might occur under action of microcapillary forces induced by removal of liquid from fluid carrier 210, when liquid is used as the fluid. For example, the small interstices, similar to small interstice 130, are arranged to capture smaller analyte molecules, for example, analyte molecules 220-1 and 220-2; and, the large interstices, similar to large interstice 132, are arranged to capture larger analyte molecules, for example, analyte molecule 410. In accordance with one or more examples of the present invention, the size of the analyte molecules captured is determined by the self-arranging spacing between the metallic caps, for example, the spacing 340 of the close-packed configuration between the metallic cap 120-1B and second metallic cap 120-2B with the analyte molecule 220-1 disposed between the metallic cap 120-1B and second metallic cap 120-2B. By way of example, in accordance with one or more examples of the present invention, the size of the self-arranging spacing may be on the order of 2 nm, without limitation thereto. Thus, in accordance with one or more examples of the present invention, the metallic-nanofinger device 101 may provide a device for the capture of analyte molecules of various sizes from a solution carrying an analyte of at least one particular molecular species. For example, the metallic-nanofinger device 101 may then be used in SERS analysis of the captured molecules of an analyte, which is subsequently described in greater detail.

Figure 5A:
FIGS. 5A, 5B and 5C are cross-sectional elevation views at various stages in the fabrication of the metallic-nanofinger device for chemical sensing of FIG. 1 illustrating a sequence of processing operations used in fabrication, in accordance with one or more examples of the present invention.
Figure 5A:
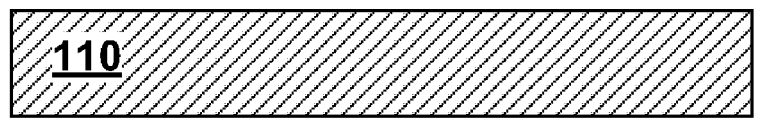
Figure 5B:
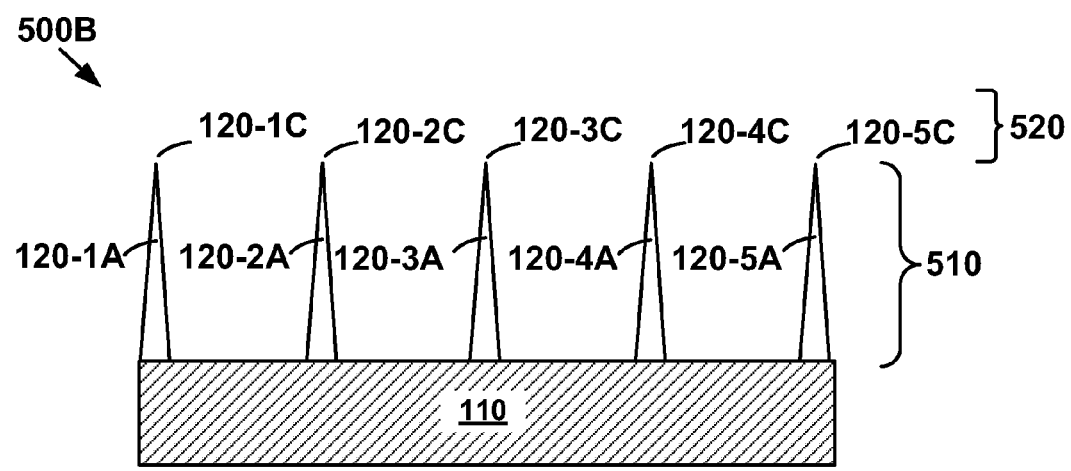
Figure 5C:
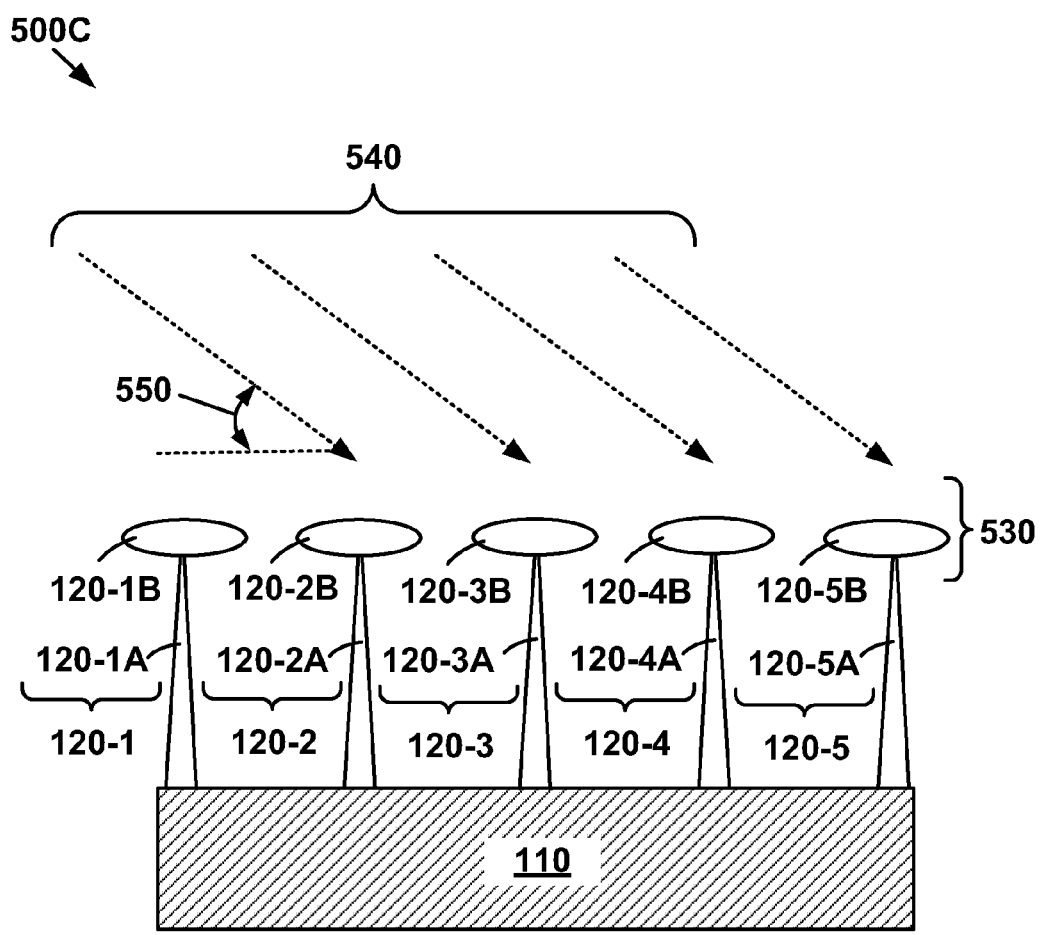

With reference now to FIGS. 5A, 5B and 5C, in accordance with yet other examples of the present invention, cross-sectional elevation views 500A, 500B and 500C, respectively, are shown of the metallic-nanofinger device 101 for chemical sensing of FIG. 1 at various stages of fabrication of the metallic-nanofinger device 101. FIGS. 5A, 5B and 5C illustrate a sequence of processing operations used in fabrication of the metallic-nanofinger device 101. FIG. 5A shows the substrate 110 upon which the rest of the structure of the metallic-nanofinger device 101 is fabricated. In accordance with one or more examples of the present invention, the substrate may be a material selected from the group consisting of silicon, glass, quartz, silicon nitride, sapphire, aluminum oxide, diamond, diamond-like carbon, one or more plastics, and one or more metals and metallic alloys. In accordance with one or more examples of the present invention, the substrate may be in a form selected from the group consisting of a sheet, a wafer, a film and a web. For example, if the substrate is in the form of a web, the substrate may be used as feed stock, as rolls of material in a roll-to-roll fabrication process. For another example, the substrate may be in the form of a flexible polymer film composed of a plastic material, such as polyimide, polyethylene, polypropylene, or some other suitable polymeric plastic. Thus, in accordance with one or more examples of the present invention, the substrate may be either rigid, as for a semiconductor wafer, or flexible, as for the web.

With further reference now to FIGS. 5B and 1, in accordance with one or more examples of the present invention, a cross-sectional elevation view 500B is shown of the metallic-nanofinger device 101 for chemical sensing of FIG. 1 at an intermediate stage of fabrication. FIG. 5B shows a plurality 510 of flexible columns, for example, flexible columns 120-1A, 120-2A, 120-3A, 120-4A and 120-5A, on the substrate 110. Each of the flexible columns of the plurality 510 of flexible columns, for example, flexible columns 120-1A, 120-2A, 120-3A, 120-4A and 120-5A, includes an apex of a plurality 520 of apices, for example, apices 120-1C, 120-2C, 120-3C, 120-4C and 120-5C. In accordance with one or more examples of the present invention, the plurality 510 of flexible columns may be produced utilizing a process selected from the group consisting of growing nanowires on the substrate 110, etching the substrate 110, nano-imprinting a coating on the substrate 110, and hot nano-embossing a coating on the substrate 110. For example, in growing nanowires to produce the flexible columns, nanowire seeds are deposited onto the substrate 110, for example, silicon; and, the nanowire is grown during chemical vapor deposition from silane. By way of another example, in etching the substrate to produce the flexible columns, a reactive ion etching (RIE) process is applied to the substrate 110, for example, silicon; and, flexible columns, for example, in the form of nanocones, without limitation thereto, are produced by removing material from the substrate 110 through the action of reactive gaseous molecules, such as, fluorine, chlorine, bromine, or a halogen molecules, in the presence of gaseous nitrogen, argon, or oxygen molecules. By way of yet another example, in nanoimprinting the substrate to produce the flexible columns, a highly viscous thin film, for example, a highly cross-linked polymer, is applied to the substrate 110, for example, in the form of a web, to produce a coating on the web; and, flexible columns, for example, in the form of nanopoles, without limitation thereto, are produced by rolling the web between a pair of rolls, one of which is a die having a relief pattern that is impressed into the highly viscous thin film coating of the web leaving a negative of the relief pattern of the die in the form of a plurality of nanopoles on the web, substrate 110. By way of yet a further example, in hot nano-embossing a coating on the substrate 110, a polymer, or plastic, is applied to the substrate 110 to produce a coating on the substrate 110; and, flexible columns, for example, in the form of nanopoles, without limitation thereto, are produced by hot embossing the coating with a die, which has a relief pattern that is impressed into the polymer, or plastic, that coats the substrate 110 leaving a negative of the relief pattern of the die in the form of a plurality of nanopoles on the substrate 110.

With further reference now to FIGS. 5C and 1, in accordance with one or more examples of the present invention, a cross-sectional elevation view 500C is shown of the metallic-nanofinger device 101 for chemical sensing of FIG. 1 nearing a final stage in fabrication. FIG. 5C shows a plurality 120 of nanofingers, for example, nanofingers 120-1, 120-2, 120-3, 120-4 and 120-5, on the substrate 110. Each of the nanofingers, for example, nanofingers 120-1, 120-2, 120-3, 120-4 and 120-5, includes the flexible column of the plurality 510 of flexible columns, for example, flexible columns 120-1A, 120-2A, 120-3A, 120-4A and 120-5A, and the metallic cap of the plurality 530 of metallic caps, for example, metallic caps 120-1B, 120-2B, 120-3B, 120-4B and 120-5B, such that each metallic cap is disposed upon an apex of the plurality 520 of apices, for example, apices 120-1C, 120-2C, 120-3C, 120-4C and 120-5C, respectively. In accordance with one or more examples of the present invention, the plurality 120 of nanofingers may be produced utilizing a process selected from the group consisting of evaporating a metallic cap, for example, metallic cap 120-1B, electroplating a metallic cap, precipitating a metallic cap from a colloidal suspension of metallic nanoparticles, lifting-off portions of a deposited metallic layer to form a metallic cap, and reducing adsorbed metalo-organic compounds by energetic particle bombardment to form a metallic cap.

For example, with further reference to FIGS. 5C and 1, in accordance with one or more examples of the present invention, in evaporating to produce the metallic caps, a stream of metal vapor 540 is produced, using thin-film vacuum-evaporation techniques, to deposit metal onto the plurality 520 of apices of the plurality 510 of flexible columns 120-1A, 120-2A, 120-3A, 120-4A and 120-5A. The plurality 530 of metallic caps 120-1B, 120-2B, 120-3B, 120-4B and 120-5B are grown from the metal vapor depositing metal onto the plurality 520 of apices 120-1C, 120-2C, 120-3C, 120-4C and 120-5C of the plurality 510 of flexible columns 120-1A, 120-2A, 120-3A, 120-4A and 120-5A. In accordance with one or more examples of the present invention, fabricating the plurality 530 of metallic caps may include evaporating metal at an angle 550 of about 30° to a surface of the substrate 110 onto the plurality 520 of apices 120-1C, 120-2C, 120-3C, 120-4C and 120-5C of the plurality 510 of flexible columns 120-1A, 120-2A, 120-3A, 120-4A and 120-5A. Moreover, in accordance with one or more examples of the present invention, the size, and consequently the spacing, of the metallic caps 120-1B, 120-2B, 120-3B, 120-4B and 120-5B can be controlled by limiting the amount of material deposited from the metallic vapor during the evaporation process.

By way of another example, with further reference to FIGS. 5C and 1, in accordance with one or more examples of the present invention, in electroplating a metallic cap, the substrate 110 including the flexible columns 120-1A, 120-2A, 120-3A, 120-4A and 120-5A is immersed in a plating solution containing metal cations. An electrical potential is applied to the substrate 110 including the flexible columns 120-1A, 120-2A, 120-3A, 120-4A and 120-5A, which results in an enhanced electrical field at the apices, for example, apex 120-1C, of the flexible columns, for example, flexible column 120-1A. The enhanced electrical field attracts the metal cations to the apices, for example, apex 120-1C, of the flexible columns, for example, flexible column 120-1A, where chemical reduction of the metal cations occurs and metal is deposited to grow the metallic caps, for example, metallic cap 120-1B.

Similarly, by way of another example, with further reference to FIGS. 5C and 1, in accordance with one or more examples of the present invention, in precipitating metallic caps from a colloidal suspension of metallic nanoparticles, the substrate 110 including the flexible columns 120-1A, 120-2A, 120-3A, 120-4A and 120-5A is immersed in a colloidal suspension of metallic nanoparticles; an electrical potential is applied to the substrate 110 including the flexible columns 120-1A, 120-2A, 120-3A, 120-4A and 120-5A, which results in an enhanced electrical field at the apices, for example, apex 120-1C, of the flexible columns, for example, flexible column 120-1A; the enhanced electrical field attracts metallic nanoparticles from the colloidal suspension to the apices, for example, apex 120-1C, of the flexible columns, for example, flexible column 120-1A, where the metallic nanoparticles are deposited to grow the metallic caps, for example, metallic cap 120-1B.

By way of yet another example, with further reference to FIGS. 5C and 1, in accordance with one or more examples of the present invention, in a lift-off process for lifting-off portions of a deposited metallic layer to produce the metallic caps, a layer of photoresist is applied to the substrate 110 including the flexible columns 120-1A, 120-2A, 120-3A, 120-4A and 120-5A. An undercut structure is produced in the photoresist adjacent to the sides of the columns, and the photoresist is etched away from the apices 120-1C, 120-2C, 120-3C, 120-4C and 120-5C of the flexible columns 120-1A, 120-2A, 120-3A, 120-4A and 120-5A. The stream of metal vapor 540 is deposited, using thin-film deposition techniques, for example, sputtering or evaporation, onto the plurality 520 of apices of the plurality 510 of flexible columns 120-1A, 120-2A, 120-3A, 120-4A and 120-5A. A thin film is deposited over the surface of the combined photoresist and partially fabricated metallic-nanofinger device 101. The photoresist and portions of the metal layer adhering to the photoresist between the flexible columns 120-1A, 120-2A, 120-3A, 120-4A and 120-5A is then removed and the plurality 530 of metallic caps 120-1B, 120-2B, 120-3B, 120-4B and 120-5B is left adhering to the plurality 520 of apices 120-1C, 120-2C, 120-3C, 120-4C and 120-5C of the plurality 510 of flexible columns 120-1A, 120-2A, 120-3A, 120-4A and 120-5A.

By way of yet a further example, with further reference to FIGS. 5C and 1, in accordance with one or more examples of the present invention, in reducing adsorbed metalo-organic compounds by energetic particle bombardment to produce the metallic caps 120-1B, 120-2B, 120-3B, 120-4B and 120-5B, the substrate 110 including the flexible columns 120-1A, 120-2A, 120-3A, 120-4A and 120-5A is exposed to a vapor of a chemical compound bearing a metal moiety, for example, a metalo-organic compound as used in chemical vapor deposition (CVD). For example, the metalo-organic compound may be provided in the form of a gas admitted to a vacuum chamber, such as, the vacuum chamber of a focused-ion beam (FIB) tool, a scanning electron microscope (SEM), or the target chamber of a laser ablation system, without limitation thereto. A suitable gas-injection system (GIS) interfaced to the vacuum chamber may be used to provide the chemical vapor bearing a metal moiety, for example, the metalo-organic compound. The gaseous vapor of the metalo-organic compound adsorbs on the surface of the substrate 110 including the apices 120-1C, 120-2C, 120-3C, 120-4C and 120-5C of the flexible columns 120-1A, 120-2A, 120-3A, 120-4A and 120-5A. An energetic beam of particles, for example, ions, electrons, or photons, without limitation thereto, irradiates the apices 120-1C, 120-2C, 120-3C, 120-4C and 120-5C of the flexible columns 120-1A, 120-2A, 120-3A, 120-4A and 120-5A. Such energetic beams of particles, for example, ions, electrons, or photons, without limitation thereto, may be provided, for example, by: the ion gun of a FIB tool, the electron gun of an SEM, or a laser of a laser ablation system, without limitation thereto. The energetic beam of particles, for example, ions, electrons, or photons, without limitation thereto, reduces the adsorbed gaseous vapor of the metalo-organic compound and grows the plurality 530 of metallic caps 120-1B, 120-2B, 120-3B, 120-4B and 120-5B onto the plurality 520 of apices 120-1C, 120-2C, 120-3C, 120-4C and 120-5C of the plurality 510 of flexible columns 120-1A, 120-2A, 120-3A, 120-4A and 120-5A.

A metallic-nanofinger device 101, as described above, can potentially provide single molecule detection and at the same time can be integrated with other optical components, such as mirrors gratings etc. to provide a chemical-analysis apparatus. However, in many fields of application of sensors, such as the metallic-nanofinger device 101, one still faces the issue of bringing the molecules, or particles, for example, analyte molecule 220-1, into proximity with the metallic-nanofinger device 101. Subsequent examples of the present invention, described herein, provide a luminescent chemical sensor 701 (see FIG. 7A-7D) integrated with at least one molecular trap 601 (see FIG. 6); the luminescent chemical sensor 701 includes at least one metallic-nanofinger device 101 and at least one molecular trap 601 such that the molecular trap 601 is to trap the analyte molecule 220-1 in proximity to at least one nanofinger 120-1 of the metallic-nanofinger device 101. Thus, a particle, or molecule, can be trapped at a trapping site in a stable position so that direct contact of the particle, or molecule, with a nanofinger 120-1 of the metallic-nanofinger device 101 is facilitated; and, sensitive detection and identification of a single analyte molecule 220-1 is made possible. Thus, the molecular trap 601 of the luminescent chemical sensor 701 is next described.

Figure 6:
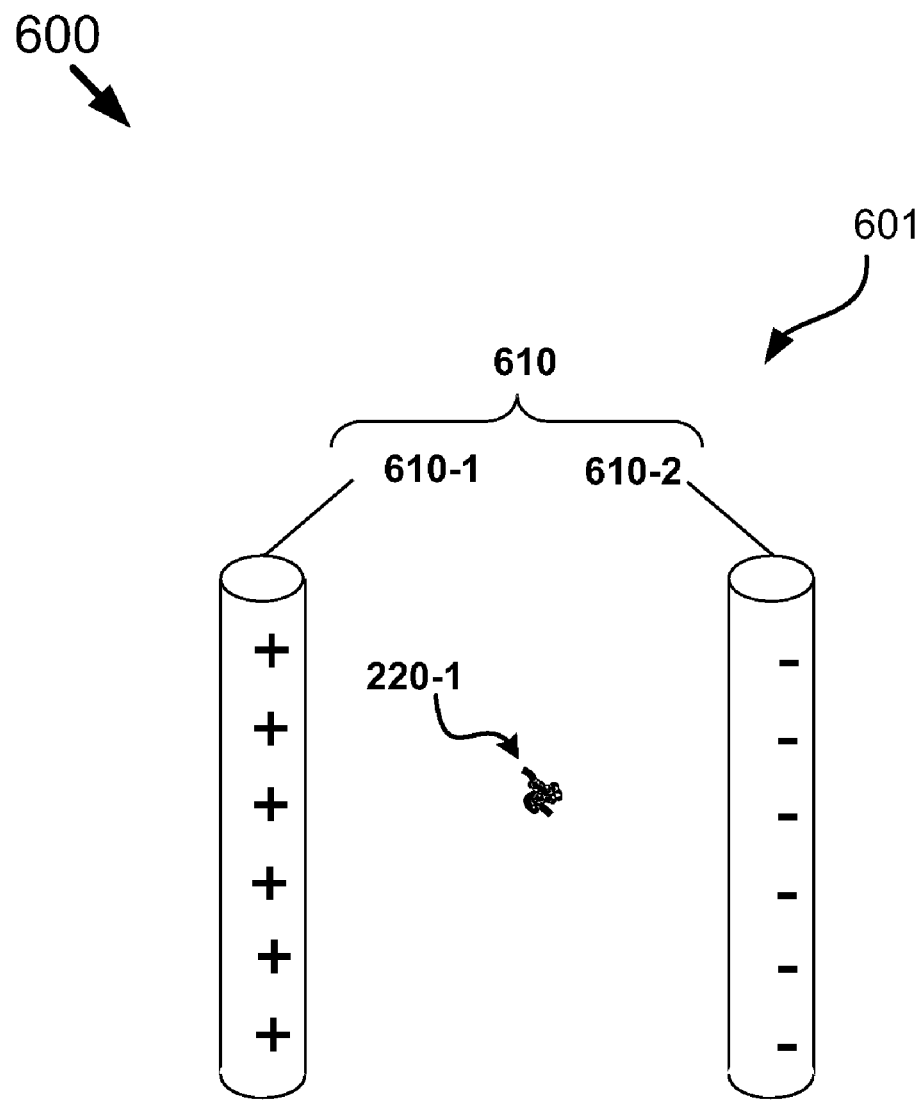
FIG. 6 is a perspective view of a molecular trap, in accordance with one or more examples of the present invention.

With reference now to FIG. 6, in accordance with one or more examples of the present invention, a perspective view 600 is shown of a molecular trap 601. As shown in FIG. 6, the molecular trap 601 includes a plurality 610 of electrodes, by way of example, a first electrode 610-1 and a second electrode 610-2, without limitation thereto. In accordance with one or more examples of the present invention, the electrodes, for example, the first and second electrodes 610-1 and 610-2, are arranged to trap at least one analyte molecule 220-1. For example, a polarizable molecule can be trapped between parallel electrodes at certain frequencies where the electric field is at its minimum. In contrast to optical tweezers, where a particle is trapped where the electromagnetic field is highest, by using a molecular trap, potential deleterious effects can be avoided that may occur upon exposure of the molecule, or particle, to high electromagnetic fields. As shown in FIG. 6, by way of example, the first electrode 610-1 has a positive potential as indicated by the plus signs; and, the second electrode 610-2 has a negative potential as indicated by the negative signs, without limitation thereto. Although this might suggest that the electric field produced between the first and second electrodes 610-1 and 610-2 is produced by a DC voltage difference applied between the first and second electrode 610-1 and 610-2, the electric field produced between the first and second electrodes 610-1 and 610-2 may also be produced by an AC voltage. In accordance with one or more examples of the present invention, the AC voltage may have a frequency selected from a range of about a kilohertz to about high megahertz.

With further reference to FIG. 6, in accordance with one or more examples of the present invention, the frequency may be selected so as to trap a particular analyte molecule 220-1. The inventors have found that molecules can be selectively trapped based upon the frequency chosen, particular analyte molecules having a characteristic frequency, similar to a resonant frequency, with which the analyte molecule may be attracted to and held at the trapping site between a plurality 610 of electrodes, for example, the first and second electrodes 610-1 and 610-2, by way of example without limitation thereto. Thus, in accordance with one or more examples of the present invention, a particular analyte molecule, for example, analyte molecule 220-1, may be trapped at the trapping site between the plurality 610 of electrodes, as well as detrapped, which is a term of art referring to the expulsion of an analyte molecule from the trapping site. Moreover, in accordance with one or more examples of the present invention, based on different designs of electrode configurations, a series of electrodes may be arranged such that, when the electric fields are modulated in various ways for various electrodes in the configuration, analyte molecules may be transported from one trapping site associated with one plurality of electrodes to another trapping site associated with another plurality of electrodes. Thus, examples of the present invention also include within their spirit and scope a plurality of electrodes including more than just the first and second electrodes 610-1 and 610-2 shown in FIG. 6. For example, a plurality of electrodes may include a configuration of multipole electrodes that are arranged to enhance the electric field between the electrodes for ease of integration and control of the location of the trapping site, where a molecule is trapped. Thus, in accordance with examples of the present invention, various configurations of the electrodes in one or more molecular traps may be combined with one or more metallic-nanofinger devices, some examples of which, without limitation thereto, are next described in FIGS. 7A-7D and 8.

Figure 7A:
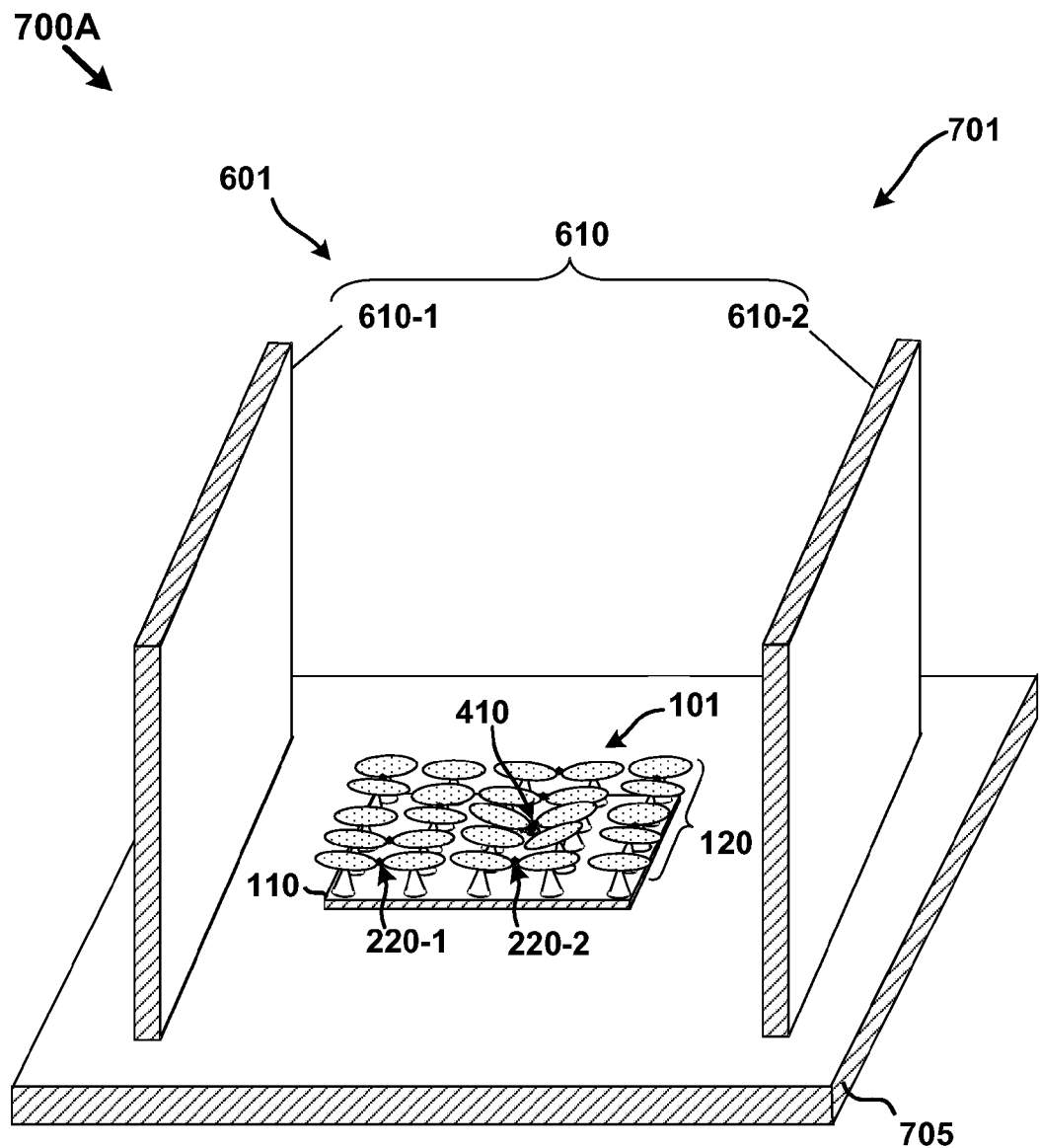
FIG. 7A is a perspective view of an example luminescent chemical sensor including the metallic-nanofinger device of FIG. 4 integrated with a molecular trap, in accordance with one or more examples of the present invention.

With reference now to FIG. 7A, in accordance with one or more examples of the present invention, a perspective view 700A is shown of an example luminescent chemical sensor 701. By way of example, the luminescent chemical sensor 701 may be integrated with at least one molecular trap 601; and, the luminescent chemical sensor 701 may include at least one metallic-nanofinger device 101 integrated with at least one molecular trap 601. The molecular trap 601 includes a plurality 610 of electrodes, for example, first and second electrodes 610-1 and 610-2. The electrodes, for example, first and second electrodes 610-1 and 610-2, are to trap at least one analyte molecule 220-1. The metallic-nanofinger device 101 includes a substrate 110, and a plurality 120 of nanofingers coupled with the substrate 110, as described above in the description of FIGS. 1-5. A nanofinger 120-1 of the plurality 120 includes a flexible column 120-1A, and a metallic cap 120-1B coupled to an apex 120-1C of the flexible column 120-1A. At least the nanofinger 120-1 and a second nanofinger 120-2 of the plurality 120 of nanofingers are to self-arrange into a close-packed configuration with at least one analyte molecule 220-1. In accordance with one or more examples of the present invention, an electric field is generated between the first and second the electrodes 610-1 and 610-2 of the plurality 610 of electrodes, for example, first and second electrodes 610-1 and 610-2, to trap the analyte molecule 220-1 in proximity to at least one nanofinger, for example, nanofinger 120-1.

By way of example, with further reference to FIG. 7A, the luminescent chemical sensor 701 may be integrated with one molecular trap 601, and may include one metallic-nanofinger device 101 integrated with the molecular trap 601, without limitation thereto. As shown in FIG. 7A, the molecular trap 601 includes a first electrode 610-1 and a second electrode 610-2. In one example of the present invention, the first and second electrodes 610-1 and 610-2 may include respective first and second plates. Moreover, the first and second plates may be disposed on another substrate 705 along with the metallic-nanofinger device 101, such that the metallic-nanofinger device 101 is disposed between the first and second plates. The plates may be arranged in a configuration similar to that of a parallel plate capacitor with the metallic-nanofinger device 101 disposed between the plates. A fluid carrying analyte molecules, for example, analyte molecules 220-1, 220-2 and 410, may flow in the space between the first and second plates. When the electrical potentials are applied to the first and second electrodes 610-1 and 610-2, corresponding to the first and second plates, by application of an AC voltage, or alternatively, a DC voltage, one or more analyte molecules may be trapped between the first and second plates in proximity to one of the metallic nanofingers, for example, metallic nanofinger 120-1, of the metallic-nanofinger device 101. Such molecules, for example, analyte molecules 220-1, 220-2 and 410, may be trapped at trapping sites from which they may be captured by one or more of the metallic nanofingers. More generally, based on different designs of electrode configurations one can fabricate a plurality 610 of electrodes on a planar substrate, similar to substrate 705, or alternatively, a non-planar substrate, such that when electric fields are generated and modulated between the plurality 610 of electrodes a trapping site may be manipulated to be disposed in proximity to the metallic-nanofinger device 101 situated on the substrate. Another configuration of electrodes of a molecular trap that may be combined with a metallic-nanofinger device is next described with the aid of FIG. 7B.

Figure 7B:
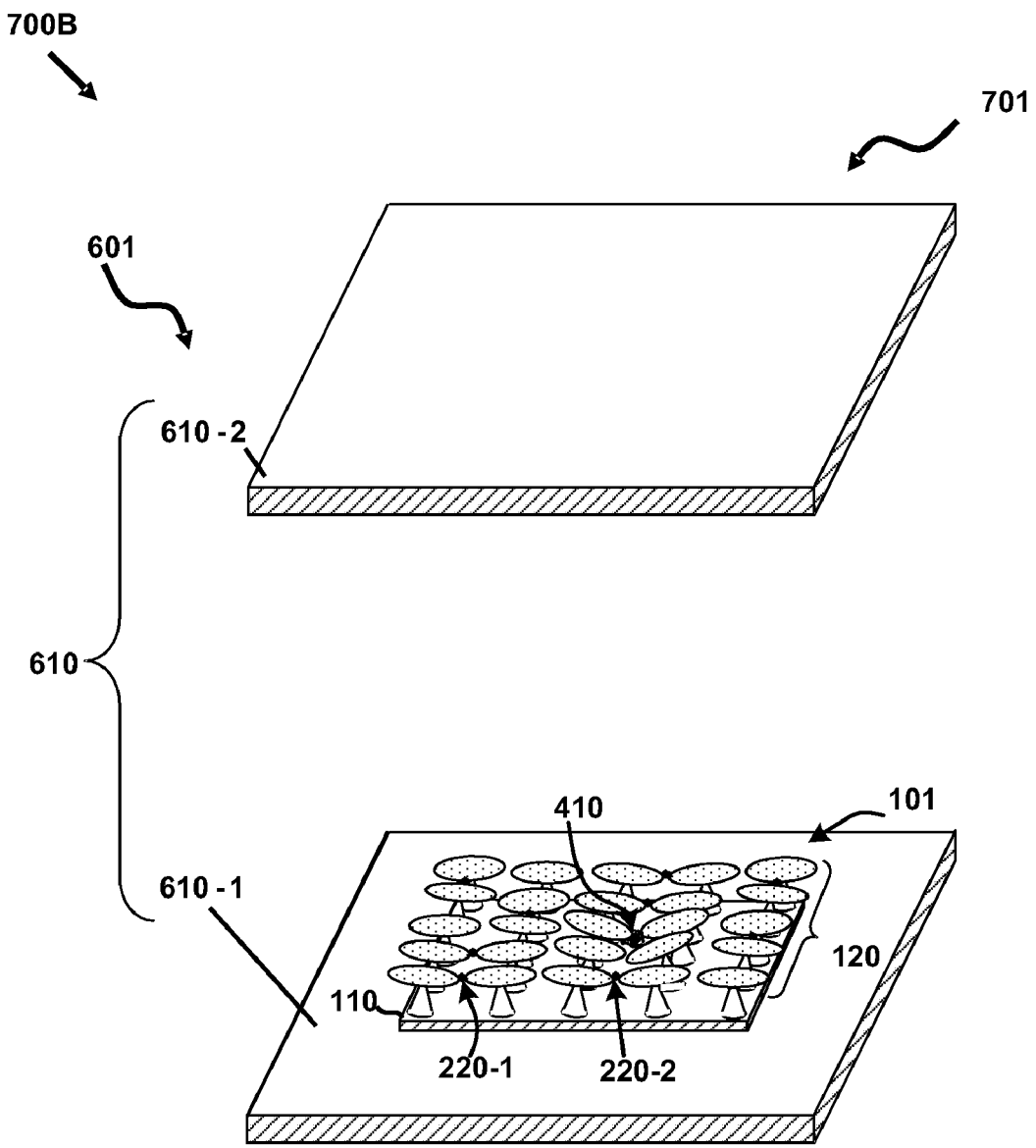
FIG. 7B is a perspective view of another example luminescent chemical sensor including the metallic-nanofinger device of FIG. 4 integrated with another example of a molecular trap, in accordance with one or more examples of the present invention.

With reference now to FIG. 7B, in accordance with one or more examples of the present invention, a perspective view 700B is shown of another example luminescent chemical sensor 701. As shown in FIG. 7B, luminescent chemical sensor 701 includes the metallic-nanofinger device 101 integrated with another example of a molecular trap 601. In accordance with one or more examples of the present invention, molecular trap 601 includes at least a first electrode 610-1 configured as a plate, and a second electrode 610-2 coupled to the substrate of the metallic-nanofinger device 101. Once again, the plates may be arranged in a configuration similar to that of a parallel plate capacitor with the metallic-nanofinger device 101 disposed between the plates; but, in this example, the metallic-nanofinger device 101 is disposed on the first electrode 610-1, corresponding to the bottom of the two plates, without limitation thereto. In accordance with one or more examples of the present invention, the first and second electrodes 610-1 and 610-2 are to trap the analyte molecule 220-1 in proximity to at least the nanofinger 120-1.

With further reference to FIG. 7B, in accordance with one or more examples of the present invention, although a metallic cap of a nanofinger, for example, nanofinger 120-1, of the plurality 120 of nanofingers may have the shape of an oblate ellipsoid, a metallic cap of a nanofinger is not limited to having the shape of an ellipsoid, as other shapes are also within the spirit and scope of examples of the present invention. In another example of the present invention, the morphology of the metallic cap 120-1B may be truncated substantially spherical such that the morphology of the cap 120-1B of the nanofinger 120-1 is similar to that of the head of a match stick, without limitation thereto. A small radius of curvature at the tip of the nanofinger will serve to increase the electric field intensity in proximity to the tip of the nanofinger, which can give rise to high intensity edge fields present at the tip. Such edge fields can serve to accumulate analyte molecules at the tip of the nanofinger in much the same fashion as an electrostatic precipitator accumulates particles. Thus, in accordance with one or more examples of the present invention, the first and second electrodes 610-1 and 610-2 are to produce an edge field on at least one metallic cap 120-1B of the nanofinger 120-1 that can serve to enhance trapping of an analyte molecule, for example, analyte molecule 220-1, in proximity to the nanofinger 120-1 of the metallic-nanofinger device 101.

Figure 7C:
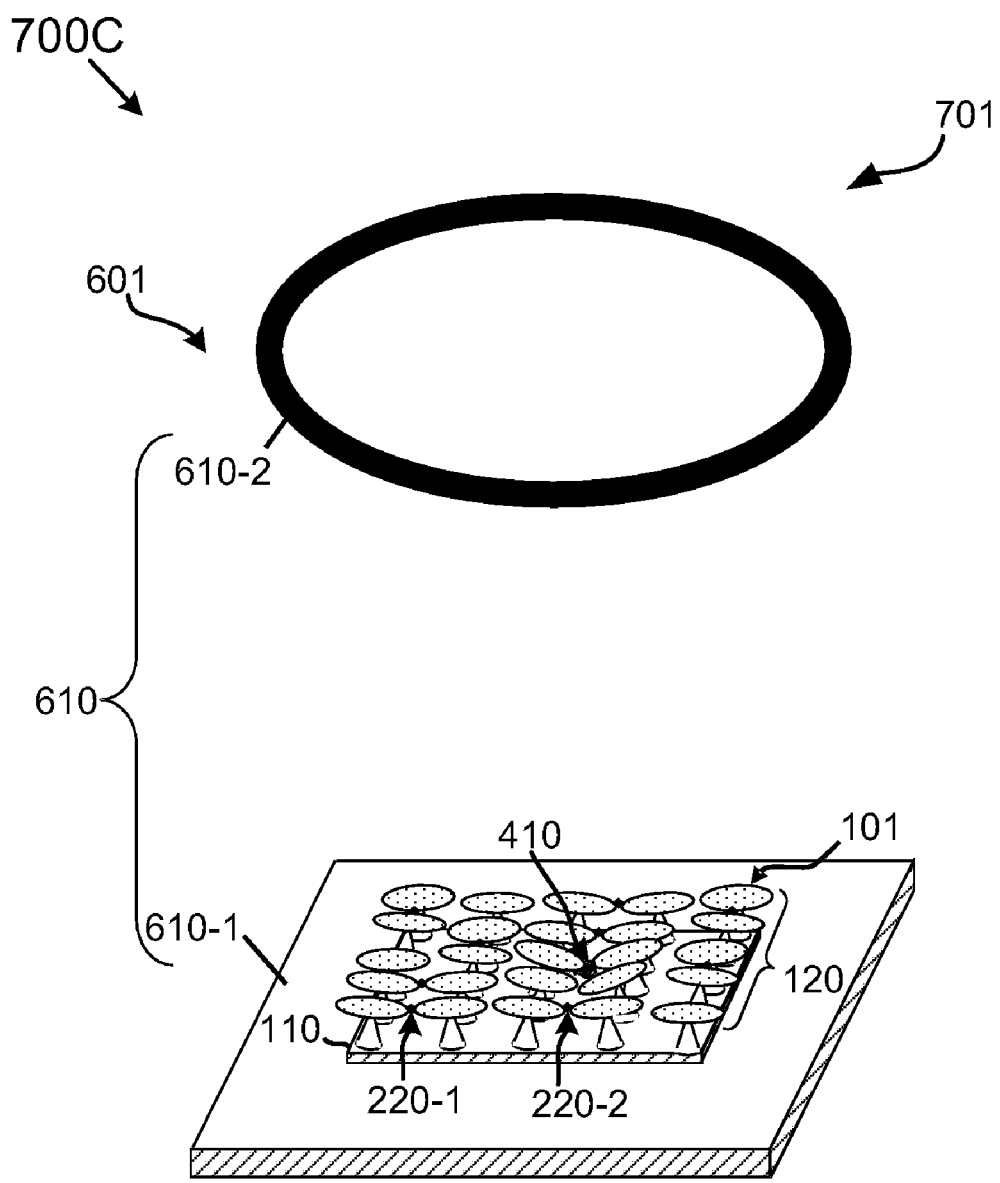
FIG. 7C is a perspective view of another example luminescent chemical sensor including the metallic-nanofinger device of FIG. 4 integrated with a molecular trap having an annular electrode, in accordance with one or more examples of the present invention.

With reference now to FIG. 7C, in accordance with one or more examples of the present invention, a perspective view 700C is shown of another example luminescent chemical sensor 701. As shown in FIG. 7C, luminescent chemical sensor 701 includes the metallic-nanofinger device 101 integrated with a molecular trap 601 having an annular electrode. In accordance with one or more examples of the present invention, at least one electrode of the plurality 610 of electrodes, for example, first and second electrodes 610-1 and 610-2, includes an annular electrode. Similar to FIG. 7B, in this example of the present invention, the metallic-nanofinger device 101 is disposed on the first electrode 610-1, corresponding to a bottom plate, without limitation thereto. In accordance with one or more examples of the present invention, the electric field may be produced by an AC voltage that is applied between the electrodes, for example, the annular electrode serving as the second electrode 610-2 and the plate serving as the first electrode 610-1. The frequency of the AC voltage may be adjusted to create a trapping site located at about a center of the annular electrode; and, the trapping site may be disposed in proximity to the nanofinger 120-1. Although in FIG. 7C the annular electrode is shown as being displaced from the tips of the plurality 120 of metallic-nanofingers of the metallic-nanofinger device 101, this is for ease of illustration, as the annular electrode may be placed in closer proximity to the metallic-nanofinger device 101. However, examples of the present invention also include a plurality 610 of electrodes including several electrodes that are displaced further away from the metallic-nanofinger device 101 than others to enhance capture and transport of an analyte molecule to the vicinity of the metallic-nanofinger device 101, as is next described.

Figure 7D:
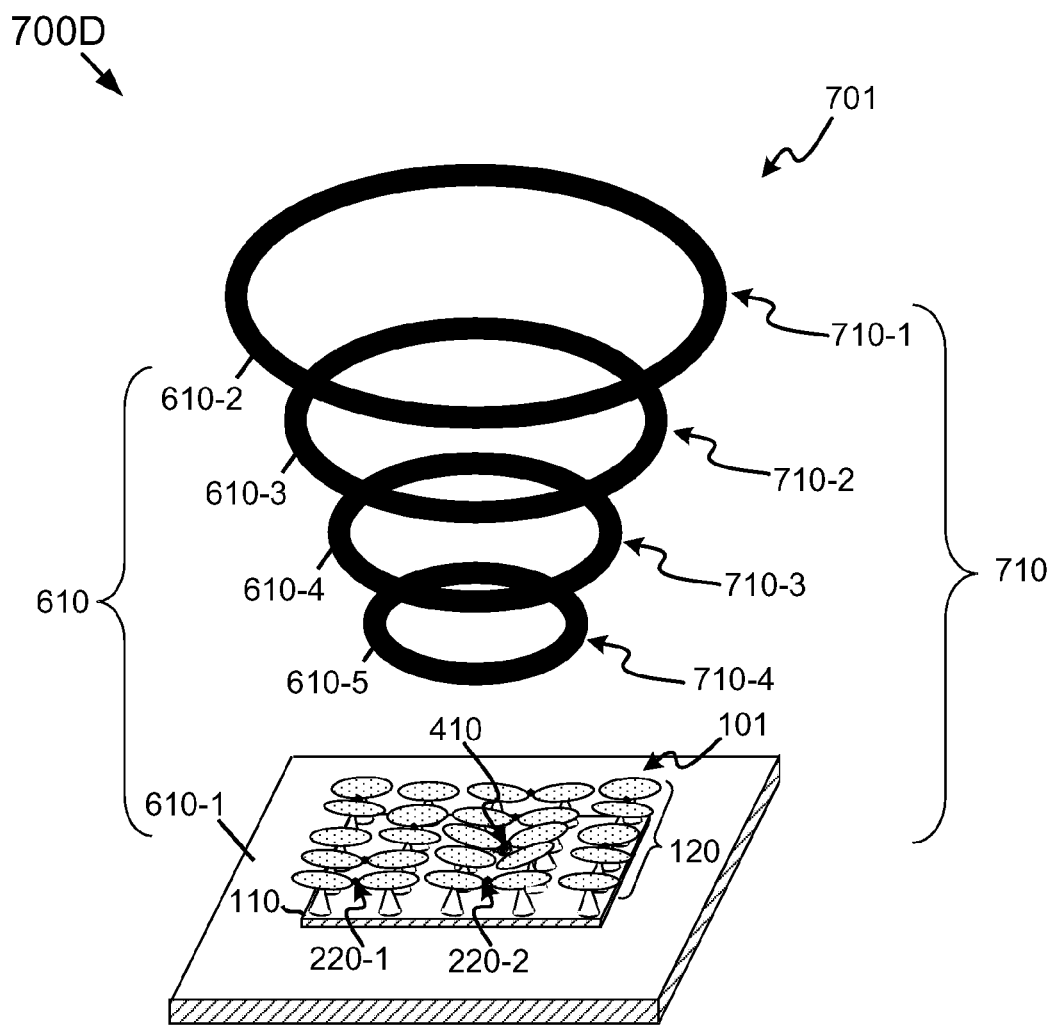
FIG. 7D is a perspective view of another example luminescent chemical sensor including the metallic-nanofinger device of FIG. 4 integrated with a plurality of molecular traps, in accordance with one or more examples of the present invention.

With reference now to FIG. 7D, in accordance with one or more examples of the present invention, a perspective view 700D is shown of another example luminescent chemical sensor 701. As shown in FIG. 7D, the luminescent chemical sensor 701 includes the metallic-nanofinger device 101 integrated with a plurality 710 of molecular traps 710-1, 710-2, 710-3 and 710-4, and at least one metallic-nanofinger device 101. As shown in FIG. 7D, the plurality 610 of electrodes 610-1, 610-2, 610-3, 610-4 and 610-5 are arranged to produce a plurality 710 of cascading molecular traps 710-1, 710-2, 710-3 and 710-4. The plurality 710 of cascading molecular traps 710-1, 710-2, 710-3 and 710-4 all have a common first electrode 610-1. Thus, molecular trap 710-1 includes first electrode 610-1 and second electrode 610-2; similarly, molecular trap 710-2 includes first electrode 610-1 and third electrode 610-3; molecular trap 710-3 includes first electrode 610-1 and fourth electrode 610-4; and, molecular trap 710-4 includes first electrode 610-1 and fifth electrode 610-5. As shown in FIG. 7D, the plurality 710 of cascading molecular traps 710-1, 710-2, 710-3 and 710-4 are shown schematically and figuratively as arranged in a funnel-like configuration, which is by way of example without limitation thereto as other pluralities of molecular traps may be arranged in alternative configurations.

With further reference to FIG. 7D, in accordance with one or more examples of the present invention, molecular trap 710-1 is disposed further from the metallic-nanofinger device 101 than the other molecular traps, and is arranged to sample a larger volume of fluid bearing analyte molecules than the other traps. By suitable manipulation of the voltage applied to molecular trap 710-1, any analyte molecules captured by the annular electrode can be passed along to the second molecular trap 710-2; and, since the second molecular trap 710-2 lies in closer proximity to the metallic-nanofinger device 101 the analyte molecules captured by molecular trap 710-1 may be transported in closer proximity to the metallic-nanofinger device 101. In similar fashion, the molecular trap 710-2 may pass analyte molecules that it has captured to the third molecular trap 710-3 yet closer to the metallic-nanofinger device 101. Next, the third molecular trap 710-3 may pass analyte molecules that it has captured to the fourth molecular trap 710-4 even closer to the metallic-nanofinger device 101. Finally, the fourth molecular trap 710-4 may pass the analyte molecules that it has captured to the metallic-nanofinger device 101, itself. Thus, in accordance with one or more examples of the present invention, the plurality 710 of molecular traps 710-1, 710-2, 710-3 and 710-4 is arranged in series to concentrate analyte molecules at the metallic-nanofinger device 101.

Although, as shown in FIG. 7D, the plurality 710 of cascading molecular traps 710-1, 710-2, 710-3 and 710-4 are shown schematically and figuratively as arranged in a funnel-like configuration, alternative configurations are also within the spirit and scope of examples of the present invention. However, these alternative configurations may also be arranged in series to concentrate analyte molecules at the metallic-nanofinger device 101. In particular, the effect of these arrangements is to increase the cross section for capturing a particular analyte molecule even to the point of being able to capture a single analyte molecule in a large volume of fluid. Thus, in accordance with examples of the present invention, the sensitivity of the luminescent chemical sensor 701 is greatly increased; and, detectability limit of the luminescent chemical sensor 701 for detection of an analyte molecule may be greatly lowered. As used herein, a lower detectability limit refers to a lesser concentration of analyte molecules in the fluid that may be detected by the luminescent chemical sensor 701. Thus, the inventors envision configurations of molecular traps, which increase the sensitivity of the luminescent chemical sensor 701 and decrease the detectability limit for the luminescent chemical sensor 701, by concentrating analyte molecules by varying the frequencies of the plurality of molecular traps to increase the capture cross-section for analyte molecules, for example, analyte molecules 220-1, 220-2 and 410.

Figure 8:
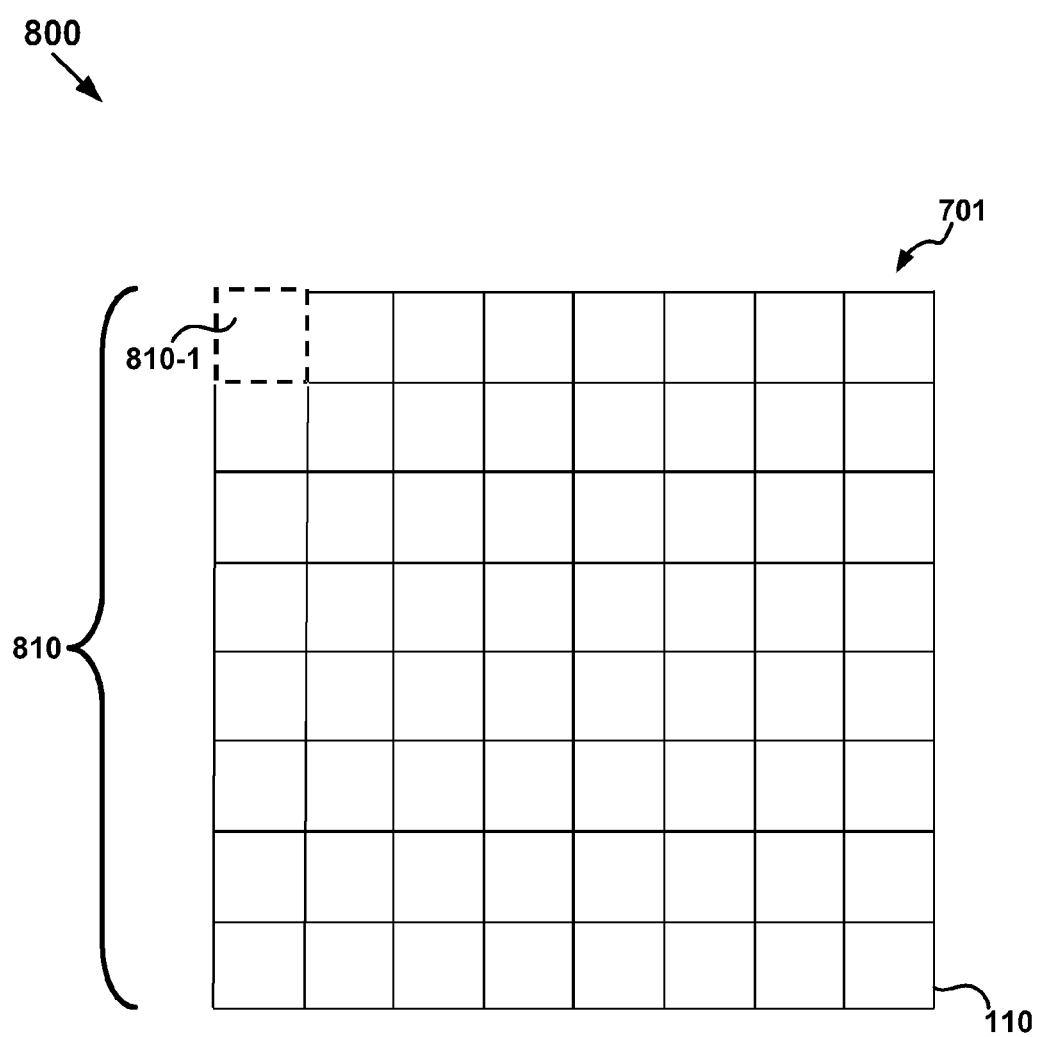
FIG. 8 is a plan view of a another example luminescent chemical sensor including a plurality of molecular traps and a plurality of metallic-nanofinger devices arranged as an array of analysis cells, in accordance with one or more examples of the present invention.

With reference now to FIG. 8, in accordance with one or more examples of the present invention, a plan view 800 is shown of another example luminescent chemical sensor 701. As shown in FIG. 7D, the luminescent chemical sensor 701 includes a plurality of molecular traps and a plurality of metallic-nanofinger devices arranged as an array 810 of analysis cells, of which analysis cell 810-1 is an example. In accordance with one or more examples of the present invention, the analysis cell 810-1 of the array 810 includes at least one metallic-nanofinger device 101 integrated with at least one molecular trap 601, similar to any of the examples of the luminescent chemical sensor 701 shown in FIGS. 7A-7C. In accordance with one or more examples of the present invention, the analysis cell 810-1 is to selectively trap an analyte molecule 220-1. Thus, the analyte molecules can be trapped or repelled at will, because the electric field can be easily modulated, as described above in the discussion of FIG. 6. For example, an analyst can examine analyte molecules, sequentially, analyte molecule by analyte molecule. The whole array 810 can be integrated inside microfluidic channels for biological studies. Different traps can be designed in the same array 810, which can selectively trap analyte molecules of a certain size and polarizability. Therefore, an array 810 of such analysis cells may provide for parallel detection of different molecular species, and well-defined transport onto, within, above, and out of analysis cells within the array 810. Moreover, the plurality of molecular traps and metallic nanofinger finger devices allows for the assembly and positioning of two or more species, for example, analyte molecules to 220-1, 220-2 and 410, with an adjustable distance down to direct contact with a metallic nanofinger, for example, metallic nanofinger 120-1.

With further reference to FIG. 8, in accordance with one or more examples of the present invention, the luminescent chemical sensor 701 may also include a second plurality 710 of molecular traps 710-1, 710-2, 710-3 and 710-4, similar to the luminescent chemical sensor 701 shown in FIG. 7D; and, by way of example, the plurality 710 of molecular traps 710-1, 710-2, 710-3 and 710-4 may be arranged in series to concentrate analyte molecules at an analysis cell, for example, analysis cell 810-1, of the array 810. Alternatively, in another example of the present invention, other pluralities of molecular traps may be arranged above one or more of the analysis cells in the array 810. The array 810 of chemical analysis cells is not necessarily coaxial or in the same plane as shown in FIG. 8. Various combinations of molecular traps and metallic-nanofinger devices are possible allowing for precise transport to and from analysis cells within the array 810. Moreover, in accordance with one or more examples of the present invention, capillary channels may be provided connecting one analysis cell to another in a daisy-chain arrangement; and, in another example of the present invention, a pump may also be utilized to transport the fluid bearing analyte molecules through these capillaries. Thus, in accordance with one or more examples of the present invention, such arrangements increase the effective flexibility and possible integration with other molecular traps and/or optical and related identification systems, for example, such as time-of-flight mass spectrometers, or more generally, a chemical-analysis apparatus 901 as next described.

Figure 9:
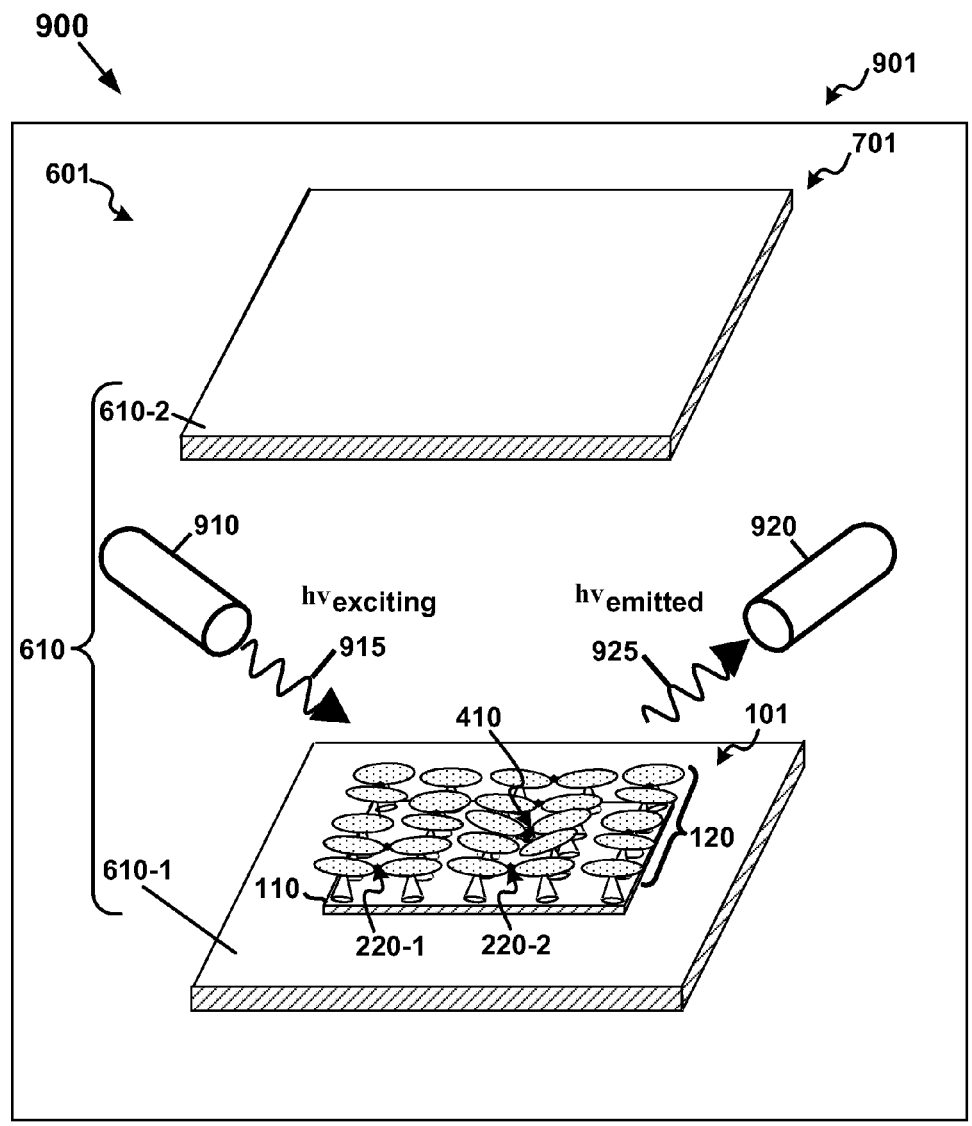
FIG. 9 is a perspective view of an example chemical-analysis apparatus including the luminescent chemical sensor of FIG. 7B, in accordance with one or more examples of the present invention.

With reference now to FIG. 9, in accordance with one or more examples of the present invention, a perspective view 900 is shown of a chemical-analysis apparatus 901 including a luminescent chemical sensor 701 integrated with a molecular trap 601 for chemical sensing. The chemical-analysis apparatus 901 includes: the luminescent chemical sensor 701 including at least one metallic-nanofinger device 101 integrated with the molecular trap 601; a source 910 of exciting electromagnetic radiation 915 to excite the analyte molecule 220-1 captured by the luminescent chemical sensor 701; and, a detector 920 to detect emitted electromagnetic radiation 925 that may be emitted from the analyte molecule 220-1 in response to the exciting electromagnetic radiation 915. The chemical-analysis apparatus 901 may also include a dispersion unit (not shown), such as a diffraction grating and slit interposed between the luminescent chemical sensor 701 and the detector 920; for such a spectroscopic configuration including a dispersion unit, the chemical-analysis apparatus 901 may selectively disperse the emitted electromagnetic radiation 925 as a function of wavelength. Alternatively, in other examples of the present invention, the chemical-analysis apparatus 901 might not be configured as a spectrometer with a dispersion unit, but as, for example, a reflectometer, without limitation thereto. The luminescent chemical sensor 701 includes the examples previously described above, as these examples may be incorporated within the environment of the chemical-analysis apparatus 901 being within the spirit and scope of examples of the present invention.

With further reference to FIG. 9 and further reference to FIGS. 1-8, in accordance with other examples of the present invention, an example configuration is shown for SERS, without limitation thereto, of analyte molecules disposed between the metallic caps of the metallic-nanofinger device 101 for chemical sensing. In accordance with one or more examples of the present invention, luminescent chemical sensor 701 may be selected from the group consisting of a mirror, a grating, a wave-guide, a microfluidic channel, a cuvette and an analysis cell any of which may be disposed in the chemical-analysis apparatus 901. In accordance with one or more examples of the present invention, the chemical-analysis apparatus 901 may include a spectrometer, for example, a Raman spectrometer, without limitation thereto. Thus, in accordance with one or more examples of the present invention, the chemical-analysis apparatus 901 may include, more generally, an instrument selected from the group consisting of a colorimeter, a reflectometer, a spectrometer, a spectrophotometer, a Raman spectrometer, an optical microscope, and an instrument that is arranged to accept the luminescent chemical sensor 701 for optical analysis and/or spectroscopic analysis.

In another example of the present invention, with further reference to FIGS. 1-9, one configuration of the chemical-analysis apparatus 901 includes a spectrometer to accept the luminescent chemical sensor 701 for performing spectroscopy, for example, SERS, of at least one molecule, for example, analyte molecule 220-1, analyte molecule 220-2, or analyte molecule 410. The spectrometer includes a source 910 of exciting electromagnetic radiation 915 that is used to excite at least one molecule, for example, analyte molecule 410. The source 910 of exciting electromagnetic radiation 915 may be a laser, without limitation thereto. The energy of a photon of the exciting electromagnetic radiation 915 is given by Planck's constant times the frequency of the laser source, given by: $h\nu_{laser}$. In addition, the spectrometer includes a dispersion unit (not shown) and a detector 920 that are used to analyze and detect emitted electromagnetic radiation 925. The emitted electromagnetic radiation 925 emerges from the analyte molecule 410 in response to the source 910 that includes an exciting laser. For example, in the case of SERS, the energy of a photon of the emitted electromagnetic radiation 925 from the analyte molecule 410 is given by Planck's constant, h, times the frequency of the molecular source, $\nu_{SERS}$, given by: $h\nu_{SERS}=h\nu_o \pm h\Delta$, where $\nu_o$ is the frequency of the incident laser field and $\Delta$ the Raman shift. Because of the interaction with surface plasmons excited in the plurality of metallic caps, for example, metallic caps 120-1B and 120-2B, metallic caps 120-3B and 120-4B, and metallic caps 120-8B, 120-9B, 120-13B and 120-14B, of the plurality of nanofingers, the magnitude of the local electric field $E_{molecule}$, at a molecule for example, analyte molecule 220-1, analyte molecule 220-2, or analyte molecule 410, respectively, is enhanced compared to the incident field $E_o$.

With further reference to FIGS. 1-9, in accordance with one or more examples of the present invention, the composition of the metallic cap is such that the surface plasmons excited in the metallic cap are within the wavelength ranges of the exciting electromagnetic radiation 915 and the electromagnetic radiation emitted from the analyte molecule 410; these wavelength ranges may extend from the near ultraviolet to the near infrared. Thus, in accordance with one or more examples of the present invention, the plurality of metallic caps may be composed of a noble metal constituent; or alternatively, the plurality of metallic caps may be composed of a constituent selected from the group of constituents consisting of copper, silver and gold. In accordance with an example of the present invention, the signal associated with the emitted electromagnetic radiation 925 is amplified by increasing the number of metallic caps in proximity to which a molecule is disposed. Examples of the present invention increase the number of metallic caps, for example, metallic caps 120-8B, 120-9B, 120-13B and 120-14B, in proximity to a molecule, for example, analyte molecule 410, by employing the plurality 120 of nanofingers including the plurality 510 (see FIG. 5B) of flexible columns upon which the plurality 530 (see FIG. 5C) of metallic caps are disposed. Thus, in accordance with one or more examples of the present invention, due to the increased number of metallic caps, an increase in the excitation of surface plasmons in proximity to the analyte molecule 410 is expected to enhance the signal from the analyte molecule 410 in SERS. Therefore, examples of the present invention provide a metallic-nanofinger device 101 that provides for surface-enhanced luminescence, for example, for SERS, without limitation thereto.

With reference now to FIG. 10A, in accordance with one or more examples of the present invention, a flowchart 1000A is shown of a method for using a luminescent chemical sensor integrated with at least one molecular trap, including at least one metallic-nanofinger device integrated with at least one molecular trap. The method for using the luminescent chemical sensor integrated with the metallic-nanofinger device for chemical sensing includes the following operations. At 1010 the luminescent chemical sensor integrated with the molecular trap is exposed to a fluid including an analyte molecule. At 1015 an electric field is generated within the molecular trap 601. At 1020 the analyte molecule is guided by the electric field into proximity with at least one nanofinger of the metallic-nanofinger device 101. At 1025 the analyte molecule 220-1 is trapped with the electric field in proximity to the nanofinger 120-1. At 1030 sufficient time is allowed for the analyte molecule to bind to the metallic cap of the nanofinger. If the fluid is a liquid, the metallic-nanofinger device may be purged of the liquid. At 1035 sufficient time is allowed for at least one nanofinger and a second nanofinger to self-arrange into a close-packed configuration with at least one analyte molecule disposed between at least one metallic cap and a second metallic cap of the respective nanofinger and second nanofinger.

Figure 10B:
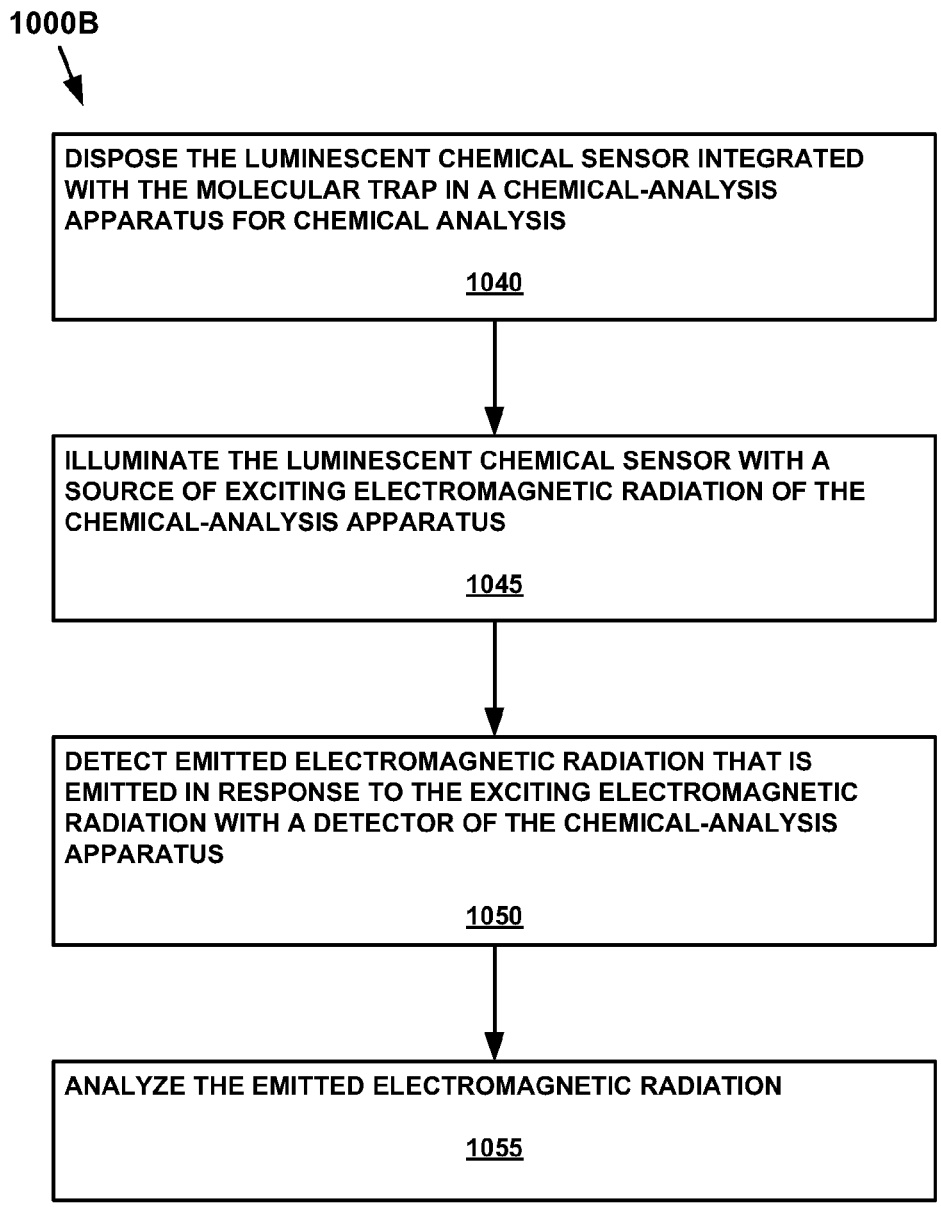
FIG. 10B is a flowchart of further operations that may be employed in the method for using the luminescent chemical sensor, in accordance with one or more examples of the present invention.

With reference now to FIG. 10B, in accordance with one or more examples of the present invention, a flowchart 1000B is shown of further operations that may be employed in the method for using a luminescent chemical sensor integrated with at least one molecular trap. The method for using the luminescent chemical sensor integrated with at least one molecular trap may further include the following operations. At 1040 the luminescent chemical sensor integrated with at least one molecular trap is disposed in a chemical-analysis apparatus for chemical analysis. At 1045 the luminescent chemical sensor is illuminated with a source of exciting electromagnetic radiation of the chemical-analysis apparatus. At 1050 emitted electromagnetic radiation is detected that is emitted in response to the exciting electromagnetic radiation with a detector of the chemical-analysis apparatus. At 1055 the emitted electromagnetic radiation is analyzed.

Examples of the present invention include a luminescent chemical sensor 701 integrated with at least one molecular trap 601 that can provide enhanced sensitivity for the presence of analyte molecules through surface-enhanced luminescence. Moreover, examples of the present invention provide for lower detectability limits in surface-enhanced luminescence of an analyte associated with an analyte molecule in solution. Examples of the present invention may also be implemented without a spectrometer, or a laser light source. On the other hand, if a Raman spectrometer is used, examples of the present invention also provide for lower detectability limits in SERS analysis of an analyte molecule. Thus, due to the enhanced sensitivity and detectability limits for molecular detection provided by examples of the present invention, the inventors expect new applications of examples of the present invention in at least medical, environmental, chemical, and biological technologies, without limitation thereto.

The foregoing descriptions of specific examples of the present invention have been presented for purposes of illustration and description. They are not intended to be exhaustive or to limit the invention to the precise forms disclosed, and many modifications and variations are possible in light of the above teaching. The examples described herein were chosen and described in order to best explain the principles of the invention and its practical application, to thereby enable others skilled in the art to best utilize the invention and various examples with various modifications as are suited to the particular use contemplated. It may be intended that the scope of the invention be defined by the claims appended hereto and their equivalents.

What is claimed is:

1. A luminescent chemical sensor integrated with at least one molecular trap, comprising:
   at least one molecular trap, said molecular trap comprising:
   a plurality of electrodes, said electrodes to trap at least one analyte molecule; and
   at least one metallic-nanofinger device integrated with said molecular trap, said metallic-nanofinger device comprising:
   a substrate; and
   a plurality of nanofingers coupled with said substrate, a nanofinger of said plurality comprising:
   a flexible column; and
   a metallic cap coupled to an said apex of said flexible column;
   wherein at least said nanofinger and a second nanofinger of said plurality of nanofingers are to self-arrange into a close-packed configuration with said analyte molecule disposed between at least said metallic cap and a second metallic cap of respective nanofinger and second nanofinger.

2. The luminescent chemical sensor of claim 1, wherein said molecular trap comprises:
   at least a first electrode and a second electrode;
   wherein said first and second electrodes are to trap said analyte molecule in proximity to at least said nanofinger.

3. The luminescent chemical sensor of claim 1, wherein said molecular trap comprises:
   at least a first electrode configured as a plate; and
   a second electrode coupled to said substrate of said metallic-nanofinger device;
   wherein said first and second electrodes are to trap said analyte molecule in proximity to at least said nanofinger.

4. The luminescent chemical sensor of claim 3, wherein said first and second electrodes are to produce an edge field on at least one said metallic cap of said nanofinger.

5. The luminescent chemical sensor of claim 1, wherein an electric field is generated between said electrodes of said plurality of electrodes to trap said analyte molecule in proximity to at least said nanofinger.

6. The luminescent chemical sensor of claim 5, wherein said electric field is produced by an AC voltage, said AC voltage having a frequency selected from a range of about a kilohertz to about high megahertz.

7. The luminescent chemical sensor of claim 5, wherein said electric field is produced by a DC voltage difference applied between at least a two electrodes of said plurality of electrodes.

8. The luminescent chemical sensor of claim 5, wherein at least one electrode of said plurality of electrodes includes an annular electrode; and said electric field is produced by an AC voltage, said AC voltage having a frequency that creates a trapping site located at a center of said annular electrode.

9. The luminescent chemical sensor of claim 1, further comprising:
   a plurality of molecular traps; and
   at least one metallic-nanofinger device;
   wherein said plurality of molecular traps is arranged in series to concentrate analyte molecules at said metallic-nanofinger device.

10. The luminescent chemical sensor of claim 1, further comprising:
    a plurality of molecular traps; and
    a plurality of metallic-nanofinger devices;
    wherein said plurality of molecular traps and said plurality of metallic-nanofinger devices are arranged as an array of analysis cells, an analysis cell of said array comprising:
    at least one metallic-nanofinger device integrated with at least one molecular trap;

wherein said analysis cell is to selectively trap an analyte molecule.

11. The luminescent chemical sensor of claim 10, further comprising:
a second plurality of molecular traps;
wherein said second plurality of molecular traps is arranged in series to concentrate analyte molecules at at least one analysis cell of said array.

12. A chemical-analysis apparatus, comprising:
a luminescent chemical sensor integrated with a molecular trap, comprising:
a molecular trap comprising:
a plurality of electrodes, said electrodes to trap a molecule; and
a metallic-nanofinger device integrated with said molecular trap for chemical sensing, said metallic-nanofinger device comprising:
a substrate; and
a plurality of nanofingers coupled with said substrate, a nanofinger of said plurality comprising:
a flexible column; and
a metallic cap coupled to an apex of said flexible column;
wherein at least said nanofinger and a second nanofinger of said plurality of nanofingers are to self-arrange into a close-packed configuration with at least one analyte molecule disposed between at least said metallic cap and a second metallic cap of respective nanofinger and second nanofinger; and a source of exciting electromagnetic radiation to excite said analyte molecule coupled with said luminescent chemical sensor; and
a detector to detect emitted electromagnetic radiation that may be emitted from said analyte molecule in response to said exciting electromagnetic radiation.

13. The chemical-analysis apparatus of claim 12, further comprising:
an instrument selected from the group consisting of a colorimeter, a reflectometer, a spectrometer, a spectrophotometer, a Raman spectrometer, an optical microscope, and an instrument to accept said luminescent chemical sensor for optical analysis.

14. The luminescent chemical sensor of claim 1, wherein a plurality of interstices is disposed between said plurality of nanofingers.

15. The chemical-analysis apparatus of claim 12, wherein a plurality of interstices is disposed between said plurality of nanofingers.

16. The luminescent chemical sensor of claim 1, further comprising:
a second molecular trap, wherein a plurality of molecular traps are arranged in series to concentrate at least one analyte molecule at an analysis cell.

17. The chemical-analysis apparatus of claim 12, further comprising:
a second molecular trap, wherein a plurality of molecular traps are arranged in series to concentrate at least one analyte molecule at an analysis cell.

* * * * *

UNITED STATES PATENT AND TRADEMARK OFFICE
CERTIFICATE OF CORRECTION

PATENT NO. : 8,404,491 B2
APPLICATION NO. : 12/916299
DATED : March 26, 2013
INVENTOR(S) : Zhiyong Li et al.

It is certified that error appears in the above-identified patent and that said Letters Patent is hereby corrected as shown below:

In the Claims

In column 20, line 10, in Claim 1, after "to an" delete "said".

In column 21, line 7, in Claim 11, delete "at at" and insert -- at --, therefor.

Signed and Sealed this
First Day of October, 2013

Teresa Stanek Rea
*Deputy Director of the United States Patent and Trademark Office*